United States Patent
Renga et al.

(10) Patent No.: US 8,598,086 B2
(45) Date of Patent: Dec. 3, 2013

(54) 3-HALO-(ARLY)-4-IMINOTETRAHYDROPICOLINATES AND THEIR USE AS HERBICIDES

(75) Inventors: James M. Renga, Indianapolis, IN (US); Paul R. Schmitzer, Indianapolis, IN (US); Gregory T. Whiteker, Carmel, IN (US); Kim E. Arndt, Carmel, IN (US); Noormohamed M. Niyaz, Indianapolis, IN (US); Christian T. Lowe, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 317 days.

(21) Appl. No.: 12/795,416

(22) Filed: Jun. 7, 2010

(65) Prior Publication Data

US 2010/0311594 A1 Dec. 9, 2010

Related U.S. Application Data

(60) Provisional application No. 61/184,871, filed on Jun. 8, 2009.

(51) Int. Cl.
*A01N 43/40* (2006.01)
*A01N 43/00* (2006.01)
*A61K 31/33* (2006.01)
*A61K 31/435* (2006.01)
*A61K 31/44* (2006.01)
*C07D 213/00* (2006.01)
*C07D 213/72* (2006.01)
*C07D 213/78* (2006.01)
*C07C 17/42* (2006.01)

(52) U.S. Cl.
USPC .......... 504/244; 504/260; 514/183; 514/277; 514/352; 514/354; 546/1; 546/304; 546/310; 570/113

(58) Field of Classification Search
USPC .......... 504/244, 260; 514/183, 277, 352, 354; 546/1, 304, 310
See application file for complete search history.

(56) References Cited

U.S. PATENT DOCUMENTS

| 6,784,137 | B2  |   | 8/2004 | Balko et al. |         |
|-----------|-----|---|--------|--------------|---------|
| 7,314,849 | B2  | * | 1/2008 | Balko et al. | 504/244 |

FOREIGN PATENT DOCUMENTS

| WO |      2007082098 A2 |  7/2007 |
|----|--------------------|---------|
| WO | PCT/US2010/037669  |  6/2010 |
| WO |      WO 2010/144379| 12/2010 |

OTHER PUBLICATIONS

Jerry March, Advanced Organic Chemistry, 1992, John Wiley & Sons, NY; 4th Ed., pp. 73, 74, 128, 470, 603, 619, 896, 942-943, 947, and 1289.*
U.S. Appl. No. 12/795,184, Applicant: James M. Renga, et al., which was filed concurrently with this application on Jun. 7, 2010.

* cited by examiner

*Primary Examiner* — Jane C Oswecki
(74) *Attorney, Agent, or Firm* — Robert Chang; Craig E. Mixan

(57) ABSTRACT

3-Halo-6-(aryl)-4-iminotetrahydropicolinic acids having mono-, di- tri- and tetra-substituted aryl substituents in the 6-position, and their acid derivatives, are herbicides demonstrating a broad spectrum of weed control.

20 Claims, No Drawings

3-HALO-(ARLY)-4-IMINOTETRAHYDROPICOLINATES AND THEIR USE AS HERBICIDES

This application claims the benefit of U.S. Provisional Application Ser. No. 61/184,871 filed on 8 Jun. 2009. This invention relates to certain 3-halo-6-(aryl)-4-iminotetrahydropicolinates and their derivatives and to the use of these compounds as herbicides.

FIELD OF THE INVENTION

Background of the Invention

A number of picolinic acids and their pesticidal properties have been described in the art. U.S. Pat. Nos. 6,784,137 B2 and 7,314,849 B2 disclose a genus of 6-aryl-4-aminopicolinic acids and their derivatives and their use as herbicides. It has now been discovered that 3-halo-6-(aryl)-4-iminotetrahydropicolinates exhibit similar herbicidal activity and selectivity.

SUMMARY OF THE INVENTION

Certain 3-halo-6-(aryl)-4-iminotetrahydropicolinic acids and their derivatives are herbicides with a broad spectrum of weed control against a variety of weeds, including grasses and broadleaves.

The invention includes compounds of Formula I:

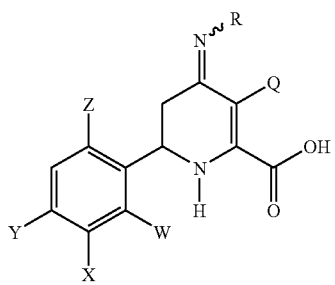

I wherein
R represents $—OS(O)_2R^1$, $—OC(O)R^1$ or $—OC(O)OR^1$;
$R^1$ represents $C_1$-$C_4$ alkyl or unsubstituted or substituted phenyl;
Q represents Cl or Br;
W represents H, F or Cl;
X represents H, F, $C_1$ or $C_1$-$C_4$ alkoxy;
Y represents halogen;
Z represents H or F; and
agriculturally acceptable derivatives of the carboxylic acid group.

Compounds of Formula I wherein W represents H or F, X represents H, F or $C_1$-$C_4$ alkoxy, Y represents Cl and Z represents H are independently preferred.

The invention includes herbicidal compositions comprising an herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

Another aspect of the invention is a process for the preparation of 3-halo-6-(aryl)-4-iminotetrahydropicolinic acid esters of the formula

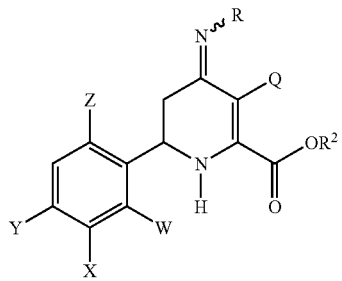

wherein
R represents $—OS(O)_2R^1$, $—OC(O)R^1$ or $—OC(O)OR^1$;
$R^1$ represents $C_1$-$C_4$ alkyl or unsubstituted or substituted phenyl;
$R^2$ represents $C_1$-$C_4$ alkyl;
Q represents Cl or Br; and
W represents H, F or Cl;
X represents H, F, $C_1$ or $C_1$-$C_4$ alkoxy;
Y represents halogen; and
Z represents H or F;
comprising the steps:
a) reacting a 4-oxo-tetrahydropicolinate of the formula

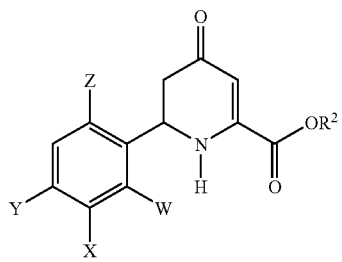

wherein W, X, Y, Z and $R^2$ are as previously defined with hydroxylamine or hydroxylamine hydrochloride in the presence of a base to provide an oxime of the formula

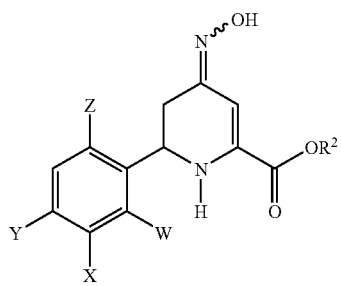

wherein W, X, Y, Z and $R^2$ are as previously defined;
b) reacting the oxime with a sulfonyl chloride, acyl chloride, alkyl chloroformate or aryl chlorofomate in the presence of a base to provide the corresponding sulfonylated, acylated or carbonate-containing oximes of the formula

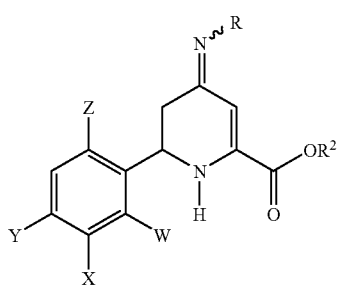

wherein W, X, Y, Z, R, $R^1$ and $R^2$ are as previously defined; and c) chlorinating or brominating the sulfonylated, acylated or carbonate-containing oxime with a chlorinating or brominating agent.

DETAILED DESCRIPTION OF THE INVENTION

The herbicidal compounds of the present invention are derivatives of 4-iminotetrahydropicolinic acids of Formula I:

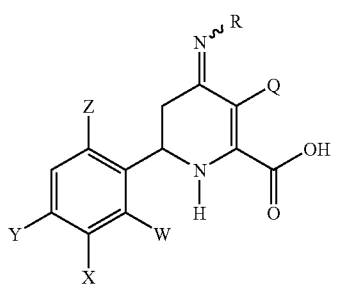

wherein

R represents $-OS(O)_2R^1$, $-OC(O)R^1$ or $-OC(O)OR^1$;
$R^1$ represents $C_1$-$C_4$ alkyl or unsubstituted or substituted phenyl;
Q represents Cl or Br;
W represents H, F or Cl;
X represents H, F, or $C_1$-$C_4$ alkoxy;
Y represents halogen;
Z represents H or F.

These compounds are characterized by possessing a carboxylic acid group or a derivative thereof in the 2-position, Cl or Br in the 3-position, a substituted imino group in the 4-position and a mono-, di-, tri- or tetra-substituted phenyl group in the 6-position of the tetrahydropyridine ring. Compounds in which Cl is in the 3-position are generally preferred. Preferred substituted phenyl groups include 2,3,4-trisubstituted, 3,4-disubstituted and 4-monosubstituted phenyl groups. Particularly preferred substituted phenyl groups include those wherein Y represents Cl, W represents H or F, X represents H, F or $C_1$-$C_4$ alkoxy and Z represents H.

The carboxylic acids of Formula I are believed to be the compounds that actually kill or control undesirable vegetation and are typically preferred. Analogs of these compounds in which the acid group of the tetrahydropicolinic acid is derivatized to form a related substituent that can be transformed within plants or the environment to an acid group possess essentially the same herbicidal effect and are within the scope of the invention. Therefore, an "agriculturally acceptable derivative," when used to describe the carboxylic acid functionality at the 2-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 3-halo-6-(aryl)-4-iminotetrahydropicolinic acid, and (b) is or can be hydrolyzed, oxidized or metabolized in plants or soil to the tetrahydropicolinic acid of Formula I that, depending upon the pH, is in the dissociated or the undissociated form. The preferred agriculturally acceptable derivatives of the carboxylic acid are agriculturally acceptable salts, esters and amides.

Suitable salts include those derived from alkali or alkaline earth metals and those derived from ammonia and amines. Preferred cations include sodium, potassium, magnesium, and aminium cations of the formula:

$R^4R^5R^6NH^+$ wherein $R^4$, $R^5$ and $R^6$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^4$, $R^5$, and $R^6$ are sterically compatible. Additionally, any two of $R^4$, $R^5$, and $R^6$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethyl-amine, morpholine, cyclododecylamine, or benzylamine Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methyl alcohol, isopropyl alcohol, 1-butanol, 2-ethylhexanol, butoxyethanol, methoxypropanol, allyl alcohol, propargyl alcohol or cyclohexanol. Esters can be prepared by coupling of the tetrahydropicolinic acid with the alcohol using any number of suitable activating agents such as those used for peptide couplings such as dicyclohexylcarbodiimide (DCC) or carbonyl diimidazole (CDI), by reacting the corresponding acid chloride of a tetrahydropicolinic acid of Formula I with an appropriate alcohol or by reacting the corresponding picolinic acid of Formula I with an appropriate alcohol in the presence of an acid catalyst. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding tetrahydropicolinic acid chloride, mixed anhydride, or carboxylic ester of Formula I with ammonia or an appropriate amine.

The term "alkyl," as well as derivative terms such as "alkoxy," as used herein, include within their scope straight chain, branched chain and cyclic moieties.

The term "unsubstituted or substituted phenyl" refers to a phenyl group that is unsubstituted or may be substituted with one or more halogen, $C_1$-$C_4$ alkyl, $C_1$-$C_4$ alkoxy or nitro groups.

Unless specifically limited otherwise, the term "halogen" including derivative terms such as "halo" refers to fluorine, chlorine, bromine and iodine. The compounds of Formula I can be made using well-known chemical procedures. The required starting materials are commercially available or readily synthesized utilizing standard procedures.

The 3-halo-6-(aryl)-4-iminotetrahydropicolinates of Formula I can be prepared in a number of ways. In step a of Scheme I, an aromatic aldehyde of Formula II, wherein W, X, Y and Z are as previously defined, can be condensed with a ketone, such as acetone, in the presence of a base, such as sodium hydroxide, to provide the α,β-unsaturated ketone of Formula III. These compounds can then be allowed to react with a base, such as sodium ethoxide, in the presence of a dialkyl oxalate to generate the β-diketoester of Formula IV as in step b, wherein $R^2$ represents $C_1$-$C_4$ alkyl, such as in U.S. Pat. No. 4,304,728. In step c of Scheme I, reaction of an amine source, such as ammonium acetate, with compounds of Formula IV results in the formation of an enamine of Formula V. Approximately a 1:2 ratio of the β-diketoester of Formula IV to the amine source is required in the reaction. The reaction is conducted at temperatures from about 25° C. to about 80° C. Temperatures from about 60° C. to about 80° C. are generally preferred. The reaction is preferably conducted in a polar protic solvent. Preferred solvents include alcohols. Either methyl alcohol or ethyl alcohol is the most preferred solvent. Finally, in step d of Scheme I, the 4-oxo-tetrahydro-picolinates of Formula VI are formed via heating of compounds of Formula V at high temperatures in a pressure vessel. The reaction is conducted at temperatures from about 125° C. to about 200° C. Temperatures from about 150° C. to about 200° C. are generally preferred. The reaction is preferably conducted in a polar aprotic solvent. Preferred solvents include ethers, such as 1,4-dioxane.

Scheme I

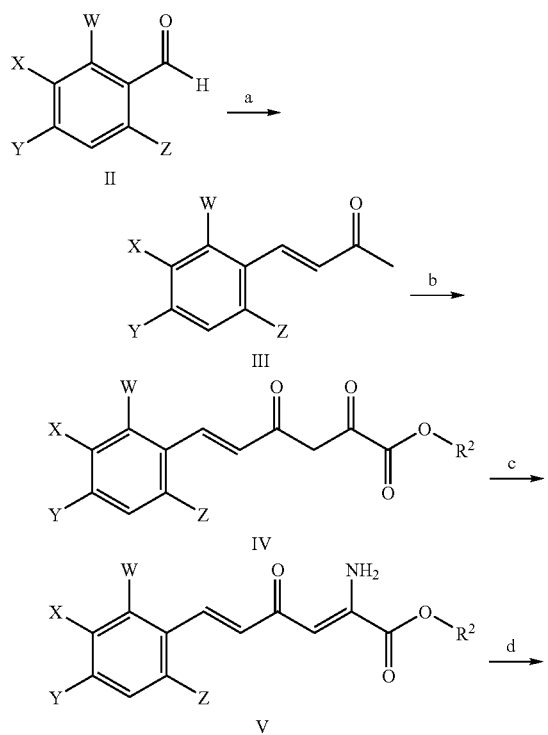

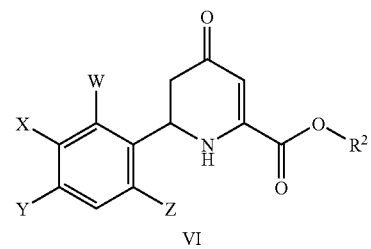

Another way to generate 4-oxo-tetrahydropicolinates of Formula VI can be found in Scheme II. In step a of Scheme II, a 2-picolinic acid is treated with thionyl chloride and an alcohol, such as methyl alcohol, to provide the 4-alkoxy-2-picolinic acid ester of Formula VII wherein $R^2$ is as previously defined. Treatment of the compounds of Formula VII with a chloroformate, followed by in situ addition of an aryl zinc halide wherein W, X, Y and Z are as previously defined, to the resulting mixture affords the dihydropicolinate of Formula VIII as shown in step b, wherein $R^3$ represents phenyl. In the first part of this two step one pot protocol, a slight excess of the chloroformate over the compound of Formula VII is required. The reaction is conducted at temperatures from about −5° C. to about 20° C. Temperatures from about −5° C. to about 10° C. are generally preferred. The reaction is preferably conducted in a polar aprotic solvent. Preferred solvents include ethers. Either tetrahydrofuran (THF) or diethyl ether is the most preferred solvent. In the second part of this step, a slight excess of the aryl zinc halide over the compound of Formula VII is required and the reaction is conducted at temperatures from about −5° C. to about 30° C. Temperatures from about 20° C. to about 30° C. are generally preferred. In step c of Scheme II, acidic hydrolysis of compounds of Formula VIII in a polar aprotic solvent, such as THF, provides the 4-oxo-tetrahydropicolinate of Formula IX protected as the carbamate. An excess of the acid over the compound of Formula VIII is required in the reaction. The reaction is conducted at temperatures from about −5° C. to about 30° C. Temperatures from about 20° C. to about 30° C. are generally preferred. The reaction is preferably conducted in polar solvent mixtures. Preferred solvents include ether-water mixtures, such as THF-water. Lastly, in step d of Scheme II, treatment of compounds of Formula IX with a base, such as sodium methoxide, followed by an aqueous workup affords the 4-oxo-tetrahydropicolinate of Formula VI. A slight excess of the base over the compound of Formula IX is required in the reaction. The reaction is conducted at temperatures from about −5° C. to about 20° C. Temperatures from about −5° C. to about 10° C. are generally preferred. The reaction is preferably conducted in a polar protic solvent. Preferred solvents include alcohols, such as methyl alcohol.

Scheme II

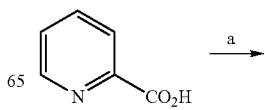

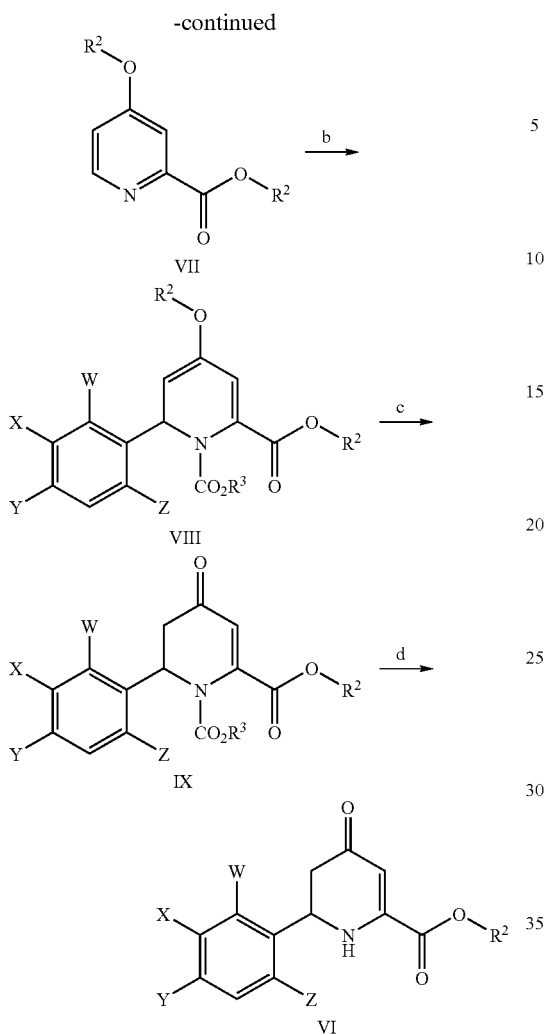

The compounds of Formula VI, wherein W, X, Y, Z and $R^2$ are as previously defined, can be converted to the corresponding oximes of Formula X by reaction with hydroxylamine or hydroxylamine hydrochloride in the presence of a base, such as pyridine, and in a solvent, such as toluene or methanol, as in step a of Scheme III. An excess of the hydroxylamine over the compound of Formula VI is required in the reaction. The reaction is conducted at temperatures from about 25° C. to about 80° C. Temperatures from about 60° C. to about 80° C. are generally preferred. The reaction is preferably conducted in a polar protic solvent. Preferred solvents include alcohols. Either methyl alcohol or ethyl alcohol is the most preferred solvent. In step b of Scheme III, the oximes of Formula X can treated with a sulfonyl chloride, acyl chloride, alkyl chloroformate or aryl chloroformate in the presence of a base to provide the corresponding sulfonylated, acylated or carbonate-containing oximes of Formula XI, where R represents —OS(O)$_2$R$^1$, —OC(O)R$^1$ and —OC(O)OR$^1$, and R$^1$ is as previously defined. An almost 2:1 ratio of the sulfonylating, acylating or carbonylating reagent over the compound of Formula X is required in the reaction. At least one equivalent of a tertiary amine base is required, with between 1 and about 2 equivalents being preferred. The reaction is conducted at temperatures from about −5° C. to about 30° C. Temperatures from about −5° C. to about 20° C. are generally preferred. Preferred solvents include inert solvents, such as chlorinated hydrocarbons. Reaction of the substituted oximes of Formula XIa with a chlorinating agent, such as sulfuryl chloride, or a brominating agent, such as bromine or N-bromosuccinimide, affords the 3-halo-(6-aryl)-4-iminotetrahydropicolinates of Formula I, wherein Q is as previously defined, as shown in step c of Scheme III. Approximately equimolar quantities of the chlorinating or brominating agent and the compound of Formula XIa are required in the reaction. The reaction is conducted at temperatures from about −5° C. to about 30° C. Temperatures from about −5° C. to about 20° C. are generally preferred. Preferred solvents include inert solvents such as dichloromethane. Alternatively, formation of compounds of Formula Ia can be accomplished by treating compounds of Formula VI in a different order—steps c, a and then b.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights-of-way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds post-emergence. It is further usually preferred to use the compounds to control a wide spectrum of broadleaf and grass weeds. Use of the compounds to control undesirable vegetation in established crops is especially indicated. While each of the 3-halo-6-(aryl)-4-iminotetrahydropicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, above and below ground plant parts such as shoots, roots, tubers, rhizomes and the like, and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I post-emergence to relatively immature undesirable vegetation to achieve the maximum control of weeds.

Application rates of about 1 to about 4,000 grams/hectare (g/ha) are generally employed in post-emergence operations; for pre-emergence applications, rates of about 1 to about 4,000 g/ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione and sulcotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; phenyl pyrazolyl ketone herbicides such as benzofenap, pyrazolynate, pyrasulfotole, pyrazoxyfen and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; fluoroalkyltriazine herbicides such as indaziflam; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone and sulfentrazone; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinone or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly the herbicidal compounds of the present invention can be used in conjunction with acetolactate synthase inhibitors on acetolactate synthase inhibitor tolerant crops.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyrdiethyl, MG 191, MON 4660, naphthalic anhydride (NA), oxabetrinil, R29148 and N-phenylsulfonylbenzoic acid amides, to enhance their selectivity.

While it is possible to utilize the 3-halo-6-(aryl)-4-iminotetrahydropicolinate compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

Example 1

Preparation of (E)-4-(4-chloro-2-fluorophenyl)-but-3-en-2-one (1)

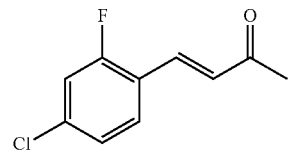

To a mechanically stirred solution of 4-chloro-2-fluorobenzaldehyde (23.8 grams (g), 0.15 mole (mol)) in acetone (100 milliliters (mL)) at room temperature was added over 20 minutes (min) a solution of sodium hydroxide (NaOH, 6.6 g, 0.165 mol) in water ($H_2O$, 400 mL). After stirring the reaction mixture overnight, dichloromethane ($CH_2Cl_2$, 100 mL) was added. The aqueous layer was separated and extracted with $CH_2Cl_2$ (100 mL), and the combined organic extracts were washed with brine and dried over magnesium sulfate ($MgSO_4$). Solvent removal followed by Kugelrohr distillation gave 4-(4-chloro-2-fluorophenyl)-3-buten-2-one (1; 22.5 g, 76%) as a colorless liquid, which solidified upon standing: by 70-80° C., 0.1 mmHg (13.33 pascals (Pa)); $^1$H NMR (400 MHz, $CDCl_3$) δ 7.59 (d, J=16.5 Hz, 1H), 7.50 (t, J=8.1 Hz, 1H), 7.22-7.12 (m, 2H), 6.76 (d, J=16.5 Hz, 1H), 2.39 (s, 3H); HRMS-ESI (m/z): calcd for $C_{10}H_8ClFO$, 198.024. found 198.025.

(E)-4-(4-Chloro-2-fluoro-3-methoxyphenyl)-but-3-en-2-one (2)

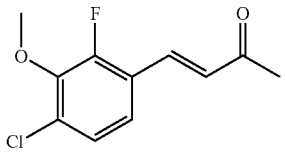

Using the procedure of Example 1,4-chloro-2-fluoro-3-methoxy-benzaldehyde (200 g, 1.6 mol), NaOH (46.6 g, 1.16 mol) and acetone (1 L) were reacted to give (E)-4-(4-chloro-2-fluoro-3-methoxyphenyl)-3-buten-2-one (2; 180 g, 74%, 93% pure by HPLC) as a pale brown liquid: $^1$H NMR (400 MHz, $CDCl_3$) δ 7.59 (d, J=16.5 Hz, 1H), 7.50 (t, J=8.1 Hz, 1H), 7.26-7.07 (m, 2H), 6.76 (d, J=16.5 Hz, 1H), 2.39 (s, 3H); HRMS-ESI (m/z): calcd for $C_{11}H_{10}ClFO_2$, 228.035. found, 228.036.

Example 2

Preparation of (E)-6-(4-chloro-2-fluorophenyl)-2,4-dioxo-hex-5-enoic acid ethyl ester (3)

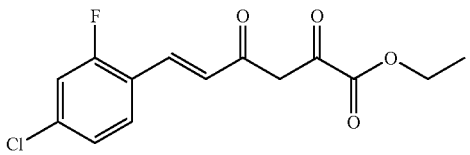 [SMILES: CCOC(=O)C(=O)CC(=O)/C=C/c1ccc(Cl)cc1F]

Sodium pellets (2.88 g, 0.125 mol) were slowly added to absolute ethyl alcohol (EtOH, 125 mL). After the sodium had reacted, the solvent was removed under reduced pressure, and anhydrous ether (200 mL) was added. The reaction mixture was cooled to −5° C., and a solution of (E)-4-(4-chloro-2-fluorophenyl)-but-3-en-2-one (1; 24.75 g, 0.125 mol) and diethyl oxalate (21.9 g, 0.15 mol) in anhydrous ether (25 mL) was added over 30 min. After stirring 2 days (d) at room temperature, the yellow solid was filtered and washed with ether. After 1 hour (h) of drying at room temperature, the solid was partitioned between $CH_2Cl_2$ (200 mL) and 1 N sulfuric acid ($H_2SO_4$, 150 mL). The organic layer was dried ($MgSO_4$), and the solvent was removed to give (E)-6-(4-chloro-2-fluoro-phenyl)-2,4-dioxo-hex-5-enoic acid ethyl ester (3; 32.3 g, 86%) as a yellow solid. A small sample was recrystallized from EtOH to yield yellow crystals: mp 84-85° C.; $^1$H NMR (400 MHz, $CDCl_3$) δ 14.72 (s, 1H), 7.76 (d, J=16.1 Hz, 1H), 7.49 (d, J=8.3 Hz, 1H), 7.24-7.12 (m, 2H), 6.73 (d, J=16.1 Hz, 1H), 6.53 (s, 1H), 4.38 (q, J=7.1 Hz, 2H), 1.40 (t, J=7.1 Hz, 3H); HRMS-ESI (m/z): calcd for $C_{14}H_{12}ClFO_4$, 298.041. found, 298.041.

(E)-6-(4-Chlorophenyl)-2,4-dioxo-hex-5-enoic acid ethyl ester (4)

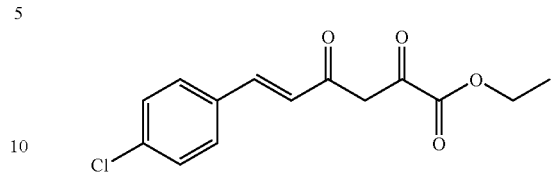

Using the procedure of Example 2, sodium pellets (6.33 g, 0.275 mol), (E)-4-(4-chlorophenye-but-3-en-2-one (45.16 g, 0.25 mol) and diethyl oxalate (43.8 g, 0.30 mol) were reacted to give (E)-6-(4-chlorophenyl-2,4-dioxo-hex-5-enoic acid ethyl ester (4; 61.1 g, 87%) as yellow crystals: mp 117-118° C.; $^1$H NMR (400 MHz, $CDCl_3$) δ 14.80 (s, 1H), 7.68 (d, J=15.9 Hz, 1H), 7.53-7.35 (m, 4H), 6.62 (d, J=15.9 Hz, 1H), 6.53 (s, 1H), 4.38 (q, J=7.2 Hz, 2H), 1.40 (t, J=7.1 Hz, 3H); HRMS-ESI (m/z): calcd for $C_{14}H_{13}ClO_4$, 280.050. found, 280.050.

(E)-6-(4-Chloro-2-fluoro-3-methoxyphenyl)-2,4-dioxo-hex-5-enoic acid ethyl ester (5)

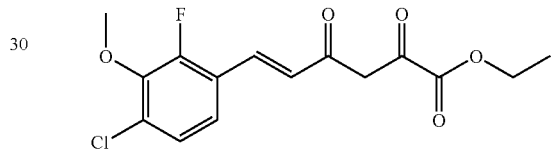

Using the procedure of Example 2, sodium pellets (5.52 g, 0.24 mol), (E)-4-(4-chloro-2-fluoro-3-methoxyphenyl)-but-3-en-2-one (2; 45.73 g, 0.20 mol) and diethyl oxalate (36.54 g, 0.25 mol) were reacted to give (E)-6-(4-chloro-2-fluoro-3-methoxyphenyl-2,4-dioxo-hex-5-enoic acid ethyl ester (5; 61.1 g, 93%) as yellow crystals: mp 67.5-69° C.; $^1$H NMR (400 MHz, $CDCl_3$) δ 14.71 (s, 1H), 7.78 (d, J=16.1 Hz, 1H), 7.27-7.18 (m, 2H), 6.73 (d, J=16.1 Hz, 1H), 6.54 (s, 1H), 4.38 (q, J=7.1 Hz, 2H), 3.99 (d, J=1.2 Hz, 3H), 1.41 (t, J=7.1 Hz, 3H); HRMS-ESI (m/z): calcd for $C_{15}H_{14}ClFNO_5$, 328.051. found, 328.051.

Example 3

Preparation of (E)-6-(4-chlorophenyl)-2,4-dioxo-hex-5-enoic acid methyl ester (6)

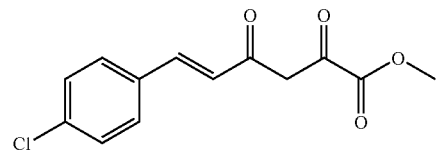 [SMILES: COC(=O)C(=O)CC(=O)/C=C/c1ccc(Cl)cc1]

A solution of (E)-6-(4-chlorophenyl)-2,4-dioxo-hex-5-enoic acid ethyl ester (4; 33.39 g, 0.12 mol) and conc $H_2SO_4$ (0.5 mL) was stirred at reflux for 6 h in methyl alcohol (MeOH, 400 mL). Upon cooling and solvent concentration, (E)-6-(4-chlorophenyl)-2,4-dioxo-hex-5-enoic acid methyl ester (6; 22.7 g, 71%) was collected as yellow crystals: mp 135-136° C.; $^1$H NMR (400 MHz, CDCl$_3$) δ 14.74 (s, 1H), 7.67 (d, J=15.9 Hz, 1H), 7.49 (d, J=8.5 Hz, 2H), 7.38 (d, J=8.5 Hz, 2H), 6.61 (d, J=15.9 Hz, 1H), 6.53 (s, 1H), 3.92 (s, 3H); HRMS-ESI (m/z): calcd for C$_{13}$H$_1$ClO$_4$, 266.034. found, 266.034.

Example 4

Preparation of (2Z,5E)-2-amino-6-(4-chloro-2-fluorophenyl)-4-oxo-hexa-2,5-dienoic acid ethyl ester (7)

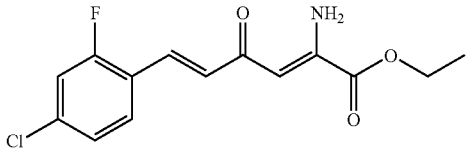 [SMILES: CCOC(=O)/C(N)=C/C(=O)/C=C/c1ccc(Cl)cc1F]

A mixture of (E)-6-(4-chloro-2-fluorophenyl)-2,4-dioxo-hex-5-enoic acid ethyl ester (3; 15.0 g, 0.05 mol) and ammonium acetate (7.7 g, 0.1 mol) in EtOH (100 mL) was stirred and heated to reflux for 1 h. The solvent was removed under reduced pressure, and the residue was dissolved in CH$_2$Cl$_2$ (200 mL) and washed with saturated aqueous sodium carbonate (Na$_2$CO$_3$, 100 mL). After drying over MgSO$_4$, silica gel (50 g) was added and the solvent was removed. The residue was washed with 20% ethyl acetate (EtOAc)/hexanes (300 mL) to give after solvent removal (2Z,5E)-2-amino-6-(4-chloro-2-fluorophenyl)-4-oxo-hexa-2,5-dienoic acid ethyl ester (7; 6.1 g, 41%) as a light orange solid: mp 102-103° C.; $^1$H NMR (400 MHz, CDCl$_3$) δ 9.4 (br s, 1H), 7.62 (d, J=15.9 Hz, 1H), 7.52 (t, J=8.5 Hz, 1H), 7.49 (d, J=8.3 Hz, 1H), 7.19-7.08 (m, 2H), 6.87 (d, J=15.9 Hz, 1H), 6.14 (s, 1H), 6.05 (br s, 1H), 4.37 (q, J=7.1 Hz, 2H), 1.39 (t, J=7.1 Hz, 3H); HRMS-ESI: calcd for C$_{14}$H$_{13}$ClFNO$_3$, 297.056. found, 297.056. Further washing of the silica gel with 40% EtOAc/hexanes (400 mL) gave more (2Z,5E)-2-amino-6-(4-chloro-2-fluorophenyl)-4-oxo-hexa-2,5-dienoic acid ethyl ester (7; 8.8 g of 70% pure by $^1$H NMR spectroscopy) for a total of 12.2 g (82%).

(2Z,5E)-2-Amino-6-(4-chlorophenyl)-4-oxo-hexa-2,5-dienoic acid ethyl ester (8)

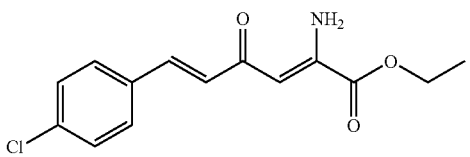 [SMILES: CCOC(=O)/C(N)=C/C(=O)/C=C/c1ccc(Cl)cc1]

Using the procedure of Example 4, (E)-6-(4-chlorophenyl)-2,4-dioxo-hex-5-enoic acid ethyl ester (4; 79.5 g, 0.284 mol) and ammonium acetate (43.78 g, 0.568 mol) were allowed to react in EtOH (795 mL) to provide (2Z,5E)-2-amino-6-(4-chlorophenyl)-4-oxo-hexa-2,5-dienoic acid ethyl ester (8; 47 g, 86%) as a yellow solid: mp 105-107° C.; $^1$H NMR (400 MHz, CDCl$_3$) δ 9.40 (br s, 1H), 7.52 (d, J=15.9 Hz, 1H), 7.50-7.47 (m, 2H), 7.38-7.32 (m, 2H), 6.78 (d, J=15.9 Hz, 1H), 6.14 (s, 1H), 6.01 (s, 1H), 4.37 (q, J=7.1 Hz, 2H), 1.39 (t, J=7.1 Hz, 3H); HRMS-ESI (m/z): calcd for C$_{14}$H$_{14}$ClNO$_3$, 279.067. found, 279.066.

(2Z,5E)-2-Amino-6-(4-chlorophenyl)-4-oxo-hexa-2,5-dienoic acid methyl ester (9)

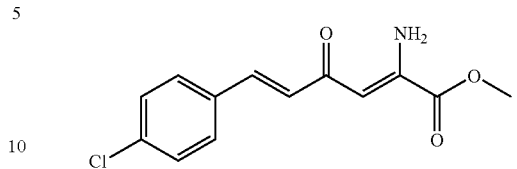

Using the procedure of Example 4, (E)-6-(4-chlorophenyl)-2,4-dioxo-hex-5-enoic acid methyl ester (6; 21.3 g, 0.008 mol) and ammonium acetate (12.33 g, 0.16 mol) were allowed to react in MeOH (150 mL) to afford (2Z,5E)-2-amino-6-(4-chlorophenyl)-4-oxo-hexa-2,5-dienoic acid methyl ester (9; 15.7 g, 74%) as a yellow solid: mp 112-113° C.; $^1$H NMR (400 MHz, CDCl$_3$) δ 9.37 (br s, 1H), 7.64-7.42 (m, 3H), 7.38-7.32 (m, 2H), 6.75 (d, J=15.9 Hz, 1H), 6.14 (s, 1H), 5.99 (br s, 1H), 3.91 (s, 3H); HRMS-ESI (m/z): calcd for C$_{13}$H$_{12}$ClNO$_3$, 265.050. found, 265.050.

2Z,5E)-2-Amino-6-(4-chloro-2-fluoro-3-methoxyphenyl)-4-oxo-hexa-2,5-dienoic acid ethyl ester (10)

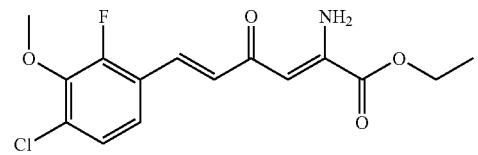 [SMILES: CCOC(=O)/C(N)=C/C(=O)/C=C/c1ccc(Cl)c(OC)c1F]

Using the procedure of Example 4, (E)-6-(4-chloro-2-fluoro-3-methoxyphenyl)-2,4-dioxo-hex-5-enoic acid ethyl ester (5; 37.8 g, 0.115 mol) and ammonium acetate (15.4 g, 0.2 mol) were allowed to react in EtOH (200 mL) to yield (2Z,5E)-2-amino-6-(4-chloro-2-fluoro-3-methoxyphenyl)-4-oxo-hexa-2,5-dienoic acid ethyl ester (10; 38.5 g, 92%, 90% pure by $^1$H NMR spectroscopy) as a dark orange solid. Treatment with silica gel (50 g) followed by eluting with 40% EtOAc/hexanes (400 mL) gave a yellow solid (25.3 g, 67%): mp 103-104° C.; $^1$H NMR (400 MHz, CDCl$_3$) δ 9.44 (br s, 1H), 7.63 (d, J=16.1 Hz, 1H), 7.23 (dd, J=8.6, 7.0 Hz, 1H), 7.16 (dd, J=8.6, 1.6 Hz, 1H), 6.87 (d, J=16.1 Hz, 1H), 6.15 (s, 1H), 6.04 (br s, 1H), 4.37 (q, J=7.1 Hz, 2H), 3.98 (d, J=1.2 Hz, 3H), 1.40 (t, J=7.1 Hz, 3H); HRMS-ESI (m/z): calcd for C$_{15}$H$_{15}$ClFNO$_4$, 327.067. found, 327.068.

Example 5

Preparation of 6-(4-chloro-2-fluorophenyl)-4-oxo-1,4,5,6-tetrahydropyridine-2-carboxylic acid ethyl ester (11)

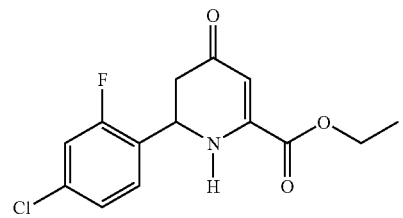 [SMILES: CCOC(=O)C1=CC(=O)CC(c2ccc(Cl)cc2F)N1]

A solution of (2Z,5E)-2-amino-6-(4-chloro-2-fluorophenyl)-4-oxo-hexa-2,5-dienoic acid ethyl ester (7; 5.26 g, 0.0177 mol) in anhydrous 1,4-dioxane (100 mL) was heated to 185° C. in a 200 mL Parr reactor under a positive nitrogen (N₂) pressure. After 9 h, the reactor was cooled, and the solvent was removed under reduced pressure leaving a dark orange oil (5.85 g). By ¹H NMR spectroscopy the material was 75% of the desired 6-(4-chloro-2-fluorophenyl)-4-oxo-1,4,5,6-tetrahydropyridine-2-carboxylic acid ethyl ester (11) along with 25% uncyclized 7. Purification on basic alumina eluting with 40% EtOAc/hexanes gave an off-white solid (1.4 g, 26%): mp 107-109° C.; ¹H NMR (400 MHz, CDCl₃) δ 7.40 (t, J=8.1 Hz, 1H), 7.22-7.06 (m, 2H), 5.84 (s, 1H), 5.73 (s, 1H), 5.09 (t, J=8.9 Hz, 1H), 4.35 (q, J=7.1 Hz, 2H), 2.69 (d, J=8.9 Hz, 2H), 1.36 (t, J=7.1 Hz, 3H); HRMS-ESI (m/z): calcd for C₁₄H₁₃ClFNO₃, 297.057. found, 297.057.

Using the procedure of Example 5, (2Z,5E)-2-amino-6-(4-chloro-2-fluoro-phenyl)-4-oxo-hexa-2,5-dienoic acid ethyl ester (7; 88 g, 0.296 mol) in 1,4-dioxane (880 mL) in a 2 liter Parr reactor gave, following purification by silica gel chromatography eluting with 40% EtOAc/hexanes, 6-(4-chloro-2-fluorophenyl)-4-oxo-1,4,5,6-tetrahydropyridine-2-carboxylic acid ethyl ester (11; 43 g, 49%, 96% pure by HPLC) as a tan solid.

6-(4-Chlorophenyl)-4-oxo-1,4,5,6-tetrahydropyridine-2-carboxylic acid ethyl ester (12)

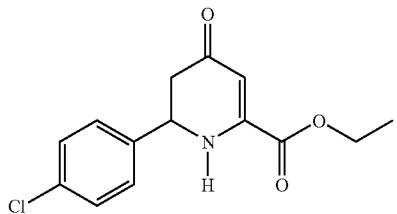 [SMILES: CCOC(=O)C1=CC(=O)CC(c2ccc(Cl)cc2)N1]

Using the procedure of Example 5, (2Z,5E)-2-amino-6-(4-chlorophenyl)-4-oxo-hexa-2,5-dienoic acid ethyl ester (8; 47 g, 0.168 mol) in 1,4-dioxane (470 mL) in a 2 liter Parr reactor gave, following purification by silica gel chromatography eluting with 40% EtOAc/hexanes, 6-(4-chlorophenyl)-4-oxo-1,4,5,6-tetrahydropyridine-2-carboxylic acid ethyl ester (12; 25 g, 49%, 99% pure by HPLC) as an off-white solid: mp 93-94° C.; ¹H NMR (400 MHz, CDCl₃) δ 7.36 (q, J=8.6 Hz, 4H), 5.82 (s, 1H), 5.72 (br s, 1H), 4.74 (dd, J=14.2, 5.0 Hz, 1H), 4.35 (q, J=7.1 Hz, 2H), 2.68 (dd, J=16.3, 14.2 Hz, 1H), 2.58 (dd, J=16.4, 5.0 Hz, 1H), 1.36 (t, J=7.1 Hz, 3H); HRMS-ESI (m/z): calcd for C₁₄H₁₄ClNO₃, 279.067. found, 279.066.

6-(4-Chlorophenyl)-4-oxo-1,4,5,6-tetrahydropyridine-2-carboxylic acid methyl ester (13)

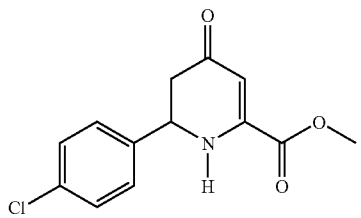 [SMILES: COC(=O)C1=CC(=O)CC(c2ccc(Cl)cc2)N1]

Using the procedure of Example 5, (2Z,5E)-2-amino-6-(4-chlorophenyl)-4-oxo-hexa-2,5-dienoic acid methyl ester (9; 6.64 g, 0.025 mol) in 1,4-dioxane (100 mL) in a 200 mL Parr reactor gave, after trituration with ether/pentane, 6-(4-chlorophenyl)-4-oxo-1,4,5,6-tetrahydropyridine-2-carboxylic acid methyl ester (13; 6.12 g, 91%, 98% pure by GC) as an off-white solid: mp 113-114° C.; ¹H NMR (400 MHz, CDCl₃) δ 7.36 (q, J=8.6 Hz, 4H), 5.82 (s, 1H), 5.72 (br s, 1H), 4.74 (dd, J=14.2, 5.0 Hz, 1H), 4.74 (dd, J=14.2, 5.0 Hz, 1H), 3.90 (s, 3H), 2.68 (dd, J=16.3, 14.2 Hz, 1H), 2.58 (dd, J=16.4, 5.0 Hz, 1H); HRMS-ESI (m/z): calcd for C₁₃H₁₂ClNO₃, 265.050. found, 265.051.

6-(4-Chloro-2-fluoro-3-methoxyphenyl)-4-oxo-1,4,5,6-tetrahydropyridine-2-carboxylic acid ethyl ester (14)

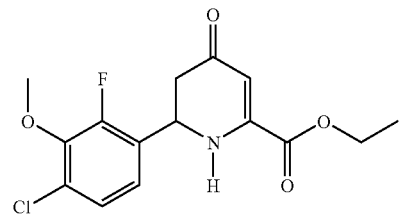 [SMILES: CCOC(=O)C1=CC(=O)CC(c2ccc(Cl)c(OC)c2F)N1]

Using the procedure of Example 5, (2Z,5E)-2-amino-6-(4-chloro-2-fluoro-3-methoxyphenyl)-4-oxo-hexa-2,5-dienoic acid ethyl ester (10; 6.55 g, 0.02 mol) in 1,4-dioxane (100 mL) in a 200 mL Parr reactor gave, after trituration with ether/pentane, 6-(4-chloro-2-fluoro-3-methoxyphenyl)-4-oxo-1,4,5,6-tetra-hydropyridine-2-carboxylic acid ethyl ester (14; 5.9 g, 90%, 98% pure by GC) as an off-white solid: mp 116-118° C.; ¹H NMR (400 MHz, CDCl₃) δ 7.22 (dd, J=8.5, 1.8 Hz, 1H), 7.09 (dd, J=8.4, 7.1 Hz, 1H), 5.93 (s, 1H), 5.90 (s, 1H), 5.21-5.08 (m, 1H), 4.37 (q, J=7.1 Hz, 2H), 3.99 (d, J=1.3 Hz, 3H), 2.87-2.73 (m, 2H), 1.38 (t, J=7.1 Hz, 3H); HRMS-ESI (m/z): calcd for C₁₅H₁₅ClFNO₄, 327.067. found, 327.067.

Example 6

Preparation of 6-(4-chloro-2-fluoro-3-methoxyphenyl)-4-oxo-5,6-dihydro-4H-pyridine-1,2-dicarboxylic acid 2-methyl ester 1-phenyl ester (15)

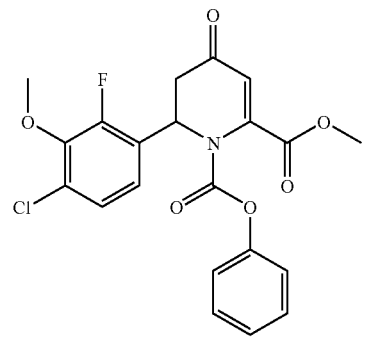 [SMILES: COC(=O)C1=CC(=O)CC(c2ccc(Cl)c(OC)c2F)N1C(=O)Oc1ccccc1]

2-Chloro-6-fluoroanisole (24.5 g, 0.153 mol) was dissolved in anhydrous THF (150 mL) under a nitrogen atmosphere. The solution was cooled to −60° C., and n-BuLi (67 mL of 2.5 M solution in hexane, 0.168 mol) was added dropwise over 30 min. During the addition the reaction warmed to −48° C. The reaction mixture was stirred for 30 min at −50° C. and then cooled to −60° C. Anhydrous $ZnCl_2$ (25 g, 0.183 mol) was added to the reaction mixture first by addition as a solid and then by addition of a solution in anhydrous THF. The reaction mixture was stirred at −45° C. for 2.5 h until nearly all of the solid $ZnCl_2$ had dissolved. The reaction solution was allowed to warm to room temperature, and solvent was evaporated by a nitrogen purge. The residue was redissolved in THF to form a stock solution.

Methyl 4-methoxypicolinate (11.92 g, 0.0713 mol) was dissolved in anhydrous THF (300 mL) under $N_2$. The solution was cooled in an ice bath. Neat phenyl chloroformate (10.5 mL, 0.0837 mol) was added. After 45 min the stock solution of (4-chloro-2-fluoro-3-methoxyphenyl)zinc(II) chloride (1.19 M in THF, 76.0 mL, 0.0904 mol) was added dropwise over 1 h. The solution was stirred at room temperature for 3 days (d) and then quenched by addition of a saturated aqueous ammonium chloride ($NH_4Cl$) solution (200 mL). The organic layer was separated, and the aqueous layer was extracted with ether (2×100 mL). The combined organic extracts were washed with $H_2O$ and then brine. The solution was dried ($MgSO_4$) and evaporated to a bright yellow liquid which was dissolved in THF (250 mL) and 1 M HCl (250 mL). The reaction mixture was stirred at room temperature for 2 d and then neutralized with saturated $NaHCO_3$ solution. The reaction mixture was extracted with ether. The ether extracts were washed with $H_2O$ followed by brine, then dried ($MgSO_4$) and evaporated to a yellow oil. The crude product was purified by silica gel chromatography (hexane-EtOAc gradient) to give a yellow oil. The oil was crystallized from MeOH to give 6-(4-chloro-2-fluoro-3-methoxyphenyl)-4-oxo-5,6-dihydro-4H-pyridine-1,2-dicarboxylic acid 2-methyl ester 1-phenyl ester (15; 17.67 g, 57%) as a white solid: mp 112-114° C.; $^1H$ NMR (300 MHz, $CDCl_3$) δ 7.40 (m, 2H), 7.27 (m, 1H), 7.14 (m, 4H), 6.22 (d, J=6.6 Hz, 1H, H6), 5.90 (d, J=1.2 Hz, 1H, H3), 3.97 (d, $J_{F-H}$=0.9 Hz, 3H, OMe), 3.87 (s, 3H, $CO_2Me$), 3.30 (dd, J=6.6, 17.4 Hz, 1H, H5a), 3.05 (d, J=18 Hz, 1H, H5b); $^{13}C\{^1H\}$ NMR (75.4 MHz, $CDCl_3$) δ 191.7 (C4), 163.8 ($CO_2Me$), 153.9 (d, $J_{F-C}$=250 Hz, C2'), 151.0, 150.3, 145.0, 144.8, 129.6 (meta Ph), 128.8 (d, $J_{F-C}$=3 Hz, C4'), 126.5 (para Ph), 125.2 (d, $J_{F-C}$=3 Hz, C5'), 124.5 (d, $J_{F-C}$=12 Hz, C1'), 121.0 (d, $J_{F-C}$=4 Hz, C6'), 120.9 (ortho Ph), 114.5 (C3), 61.6 (d, $J_{F-C}$=5 Hz, OMe), 53.8, 53.4, 41.6; Anal. Calcd for $C_{21}H_{17}ClFNO_6$: C, 58.14; H, 3.95; N, 3.23. Found: C, 57.82; H, 3.90; N, 3.18.

Example 7

Preparation of 6-(4-chloro-2-fluoro-3-methoxyphenyl)-4-oxo-1,4,5,6-tetrahydropyridine-2-carboxylic acid methyl ester (16)

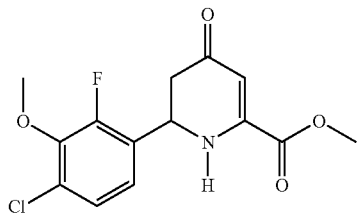 [SMILES: COC(=O)C1=CC(=O)CC(c2ccc(Cl)c(OC)c2F)N1]

6-(4-Chloro-2-fluoro-3-methoxyphenyl)-4-oxo-5,6-dihydro-4H-pyridine-1,2-dicarboxylic acid 2-methyl ester 1-phenyl ester (15; 7.213 g, 0.0166 mol) was slurried in MeOH (80 mL). The suspension was cooled in an ice bath, and solid sodium methoxide (NaOMe; 1.08 g, 0.02 mol) was added. After 1 h, the reaction was quenched with saturated aqueous $NH_4Cl$ solution (80 mL) and $H_2O$ (50 mL) and then cooled in ice. The precipitate was filtered, washed with $H_2O$ followed by cold MeOH and dried in air to give 6-(4-chloro-2-fluoro-3-methoxyphenyl)-4-oxo-1,4,5,6-tetrahydropyridine-2-carboxylic acid methyl ester (16; 4.93 g, 94%) as a white powder: mp 164.9-166.2° C.; $^1H$ NMR (300 MHz, $CDCl_3$) δ 7.20 (dd, $J_{F-H}$=1.8 Hz, $J_{H-H}$=8.7 Hz, 1H, aromatic), 7.10 (dd, $J_{F-H}$=6.9 Hz, $J_{H-H}$=8.7 Hz, 1H, aromatic), 5.84 (d, J=0.9 Hz, 1H, H3), 5.68 (br s, 1H, NH), 5.10 (t, J=9.3 Hz, 1H, H6), 3.98 (d, $J_{F-H}$=1.5 Hz, 3H, OMe), 3.91 (s, 3H, $CO_2Me$), 2.71 (d, J=9 Hz, 2H, H5); $^{13}C\{^1H\}$ NMR (75.4 MHz, $CDCl_3$) δ 193.0 (C4), 163.6 ($CO_2Me$), 153.8 (d, $J_{F-C}$=251 Hz, C2'), 147.9 (C2), 144.6 (d, $J_{F-C}$=13 Hz, C3'), 128.6 (d, $J_{F-C}$=3 Hz, C1'/C4'), 126.8 (d, $J_{F-C}$=11 Hz, C1'/C4'), 125.5 (d, $J_{F-C}$=3 Hz, C5'), 121.5 (d, $J_{F-C}$=4 Hz, C6'), 102.0 (C3), 61.6 (d, $J_{F-C}$=5 Hz, OMe), 53.4, 50.8, 42.0; HRMS-ESI (m/z): calcd for $C_{14}H_{13}ClFNO_4$, 313.0512. found, 313.0511. Anal. Calcd for $C_{14}H_{13}ClFNO_4$: C, 53.60; H, 4.18; N, 4.46. Found: C, 53.30; H, 4.14; N, 4.35.

Example 8

Preparation of 6-(4-chloro-2-fluorophenyl)-4-hydroxyimino-L4,5,6-tetrahydropyridine-2-carboxylic acid ethyl ester (17)

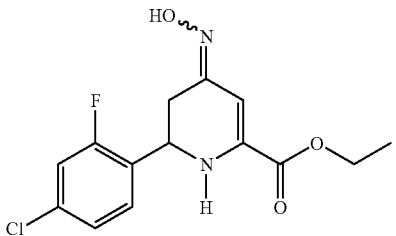 [SMILES: CCOC(=O)C1=CC(=NO)CC(c2ccc(Cl)cc2F)N1]

A mixture of 6-(4-chloro-2-fluorophenyl)-4-oxo-1,4,5,6-tetrahydropyridine-2-carboxylic acid ethyl ester (11, 41 g, 0.138 mol), hydroxylamine hydrochloride (38.3 g, 0.552 mol), and pyridine (82 mL) in EtOH (400 mL) was heated to reflux for 1 h. The reaction mixture was cooled to room temperature and the solvent was removed. The residue was triturated with ice-cold $H_2O$ to give a 3:2 mixture of syn and anti isomers of 6-(4-chloro-2-fluorophenyl)-4-hydroxyimino-1,4,5,6-tetrahydropyridine-2-carboxylic acid ethyl ester (17; 24 g, 56%, 98% pure by HPLC) as a tan solid: mp 124-126° C.; $^1H$ NMR (400 MHz, DMSO-$d_6$) major isomer δ 9.3 (br s, 1H), 7.40 (m, 1H), 7.27 (m, 2H), 6.76 (br s, 1H), 6.21 (s, 1H), 4.80 (br s, 1H), 4.42-4.13 (m, 2H), 2.69 (dd, J=14.9, 4.9 Hz, 1H), 2.62-2.45 (m, 1H), 1.30 (t, J=6.8 Hz, 3H); $^1H$ NMR (400 MHz, DMSO-$d_6$) minor isomer δ 9.3 (br s, 1H), 7.40 (m, 1H), 7.27 (m, 2H), 6.12 (br s, 1H), 5.95 (s, 1H), 4.64 (dd, J=8.4, 5.1 Hz, 1H), 4.42-4.13 (m, 2H), 2.91 (dd, J=16.5, 4.9 Hz, 1H), 2.52 (m, 1H), 1.27 (t, J=6.5 Hz, 3H); HRMS-ESI (m/z): calcd for $C_{14}H_{14}ClFN_2O_3$, 312.068. found, 312.067.

6-(4-Chloro-2-fluoro-3-methoxyphenyl)-4-hydroxy-imino-L4,5,6-tetrahydropyridine-2-carboxylic acid methyl ester (18)

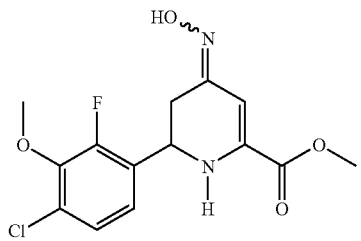 [SMILES: COC(=O)C1=CC(=NO)CC(c2ccc(Cl)c(OC)c2F)N1]

6-(4-Chloro-2-fluoro-3-methoxyphenyl)-4-oxo-1,4,5,6-tetrahydropyridine-2-carboxylic acid methyl ester (16, 5.19 g, 16.5 mmol) was slurried in methanol (160 mL).

Hydroxylamine hydrochloride (3.35 g, 48.3 mmol) was added, followed by pyridine (10.0 mL, 123 mmol). The reaction mixture was stirred at reflux for 120 min. Methanol was evaporated under vacuum. $H_2O$ (200 mL) was added, and the residue was extracted into ether (4×150 mL). The combined extracts were washed with brine, dried ($MgSO_4$) and evaporated under vacuum to give 6-(4-chloro-2-fluoro-3-methoxyphenyl)-4-hydroxyimino-1,4,5,6-tetrahydro-pyridine-2-carboxylic acid methyl ester (18; 4.54 g, 80%) as a white solid: mp 136-138° C. A 1:1 mixture of syn and anti isomers was observed by NMR spectroscopy and HPLC. $^1$H NMR (400 MHz, $C_6D_6$) δ 8.34 (br, 1H, NOH), 8.25 (br, 1H, NOH), 7.00 (s, 1H, H3), 6.71 (dd, $J_{F-H}$=1.5 Hz, $J_{H-H}$=9 Hz, 1H, aromatic), 6.69 (dd, $J_{F-H}$=1.8 Hz, $J_{H-H}$=9 Hz, 1H, aromatic), 6.57 (dd, $J_{F-H}$=$J_{H-H}$=7.5 Hz, 1H, aromatic), 6.53 (s, 1H, H3), 6.50 (dd, $J_{F-H}$=$J_{H-H}$=7.5 Hz, 1H, NH), 4.72 (s, 1H, NH), 4.52 (s, 1H, NH), 4.38 (dd, $J_{H-H}$=3.6, 10.2 Hz, 1H, H6, isomer A), 4.23 (dd, $J_{H-H}$=3.9, 11.4 Hz, 1H, H6, isomer B), 3.53 (s, 6H, $CO_2Me$), 3.24 (s, 3H, OMe), 3.23 (s, 3H, OMe), 3.30 (dd, $J_{H-H}$=4.2, 16.8 Hz, 1H, H5, isomer B), 2.63 (dd, $J_{H-H}$=4.2, 15.3 Hz, 1H, H5, isomer A), 2.44 (dd, $J_{H-H}$=10.5, 15.3 Hz, 1H, H5, isomer A), 2.33 (dd, $J_{H-H}$=11.1, 16.8 Hz, 1H, H5, isomer B); $^{13}$C {$^1$H} NMR ($CDCl_3$) δ 164.2 ($CO_2Me$), 163.9 ($CO_2Me$), 153.7 (d, $J_{F-C}$=250 Hz, C2'), 153.6 (d, $J_{F-C}$=251 Hz, C2'), 152.6 (C4), 149.6 (C4), 144.3 (d, $J_{F-C}$=3 Hz, C3'), 144.1 (d, $J_{F-C}$=3 Hz, C3'), 139.2, 138.3, 128.6 (d, $J_{F-C}$=12 Hz), 127.9 (d, $J_{F-C}$=11 Hz), 127.8 (d, $J_{F-C}$=3 Hz), 127.7 (d, $J_{F-C}$=3 Hz), 125.3, 121.7, 101.7 (C3), 92.6 (C3), 61.42, 61.38, 52.7, 52.6, 49.3, 48.3, 33.6 (C5), 28.7 (C5). HRMS-ESI (m/z) calcd for $C_{14}H_{14}ClFN_2O_4$, 328.0621. found, 328.0620. Anal. Calcd for $C_{14}H_{14}ClFN_2O_4$: C, 51.15; H, 4.29; N, 8.52. Found: C, 51.31; H, 4.34; N, 8.40.

Example 9

Preparation of 6-(4-chlorophenyl)-4-hydroxyimino-1,4,5,6-tetrahydropyridine-2-carboxylic acid ethyl ester (19)

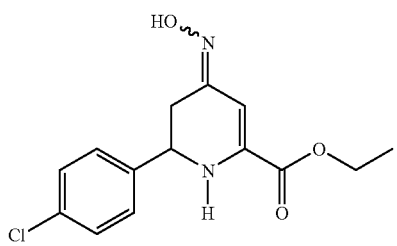 [SMILES: CCOC(=O)C1=CC(=NO)CC(c2ccc(Cl)cc2)N1]

A mixture of 6-(4-chlorophenyl)-4-oxo-1,4,5,6-tetrahydropyridine-2-carboxylic acid ethyl ester (12; 5.6 g, 0.02 mol) and 50% aqueous hydroxylamine (3 mL, 0.045 mol) in toluene (100 mL) was stirred at reflux for 2 h. After solvent removal the residue was added to $CH_2Cl_2$ (100 mL), washed with a saturated aqueous solution of NaCl, dried ($MgSO_4$), and the solvent was removed to give an orange solid (5.8 g). Trituration with ether/pentane gave a 3:2 mixture of syn and anti isomers of 6-(4-chlorophenyl)-4-hydroxyimino-1,4,5,6-tetrahydropyridine-2-carboxylic acid ethyl ester (19; 4.85 g, 85%) as an off-white solid: mp 159-160° C.; $^1$H NMR (400 MHz, $CDCl_3$) major isomer δ 9.3 (br, 1H), 7.35-7.25 (m, 4H), 6.19 (s, 1H), 4.88 (s, 1H), 4.36-4.25 (m, 3H), 3.35-3.23 (m, 1H), 2.35 (dd, J=16.8, 12.8 Hz, 1H), 1.34 (t, J=7.1 Hz, 3H); $^1$H NMR (400 MHz, $CDCl_3$) minor isomer δ 9.3 (br s, 1H), 7.35-7.25 (m, 4H), 6.57 (s, 1H), 5.19 (s, 1H), 4.57-4.38 (m, 1H), 4.36-4.25 (m, 2H), 2.72-2.54 (m, 2H), 1.34-1.31 (m, 3H); HRMS-ESI (m/z): calcd for $C_{14}H_{15}ClN_2O_3$, 294.077. found, 294.077.

Example 10

Preparation of 6-(4-chloro-2-fluorophenyl)-4-[(E,Z)-methanesulfonyloximino]-1,4,5,6-tetrahydropyridine-2-carboxylic acid ethyl ester (20)

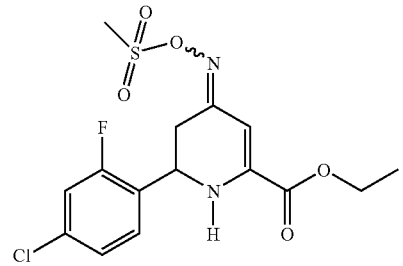 [SMILES: CCOC(=O)C1=CC(=NOS(C)(=O)=O)CC(c2ccc(Cl)cc2F)N1]

To a magnetically-stirred solution of 6-(4-chloro-2-fluorophenyl)-4-hydroxyimino-1,4,5,6-tetrahydropyridine-2-carboxylic acid ethyl ester (17; 22.0 g, 0.0705 mol) in $CH_2Cl_2$ (220 mL) was added triethylamine (19.6 mL, 0.141 mol). The reaction mixture was cooled in an ice bath and methanesulfonyl chloride (8.8 mL, 0.113 mol) was added dropwise over 30 min. Upon warming to room temperature overnight, the reaction mixture was diluted with $CH_2Cl_2$ (200 mL), washed with saturated aqueous solutions of $NaHCO_3$ and NaCl, and dried ($Na_2SO_4$). Solvent removal followed by trituration with ether/pentane gave an 8:1 mixture of isomers of 6-(4-chloro-2-fluorophenyl)-4-[(E,Z)-methanesulfonyl-oximino]-1,4,5,6-tetrahydropyridine-2-carboxylic acid ethyl ester (20; 10.5 g, 39%, 95% pure by $^1$H NMR) as an off-white solid: mp 114-116° C.; $^1$H NMR (400 MHz, $CDCl_3$) major isomer δ 7.36 (t, J=8.1 Hz, 1H), 7.19 (dd, J=8.3, 1.6 Hz, 1H), 7.15 (dd, J=10.1, 1.9 Hz, 1H), 6.37 (s, 1H), 5.59 (s, 1H), 4.93 (dd, J=10.9, 4.4 Hz, 1H), 4.35 (q, J=7.1 Hz, 2H), 3.15 (s, 3H), 2.92-2.68 (m, 2H), 1.38 (t, J=7.1 Hz, 3H); HRMS-ESI (m/z): calcd for $C_{15}H_{16}ClFN_2O_5S$, 390.0447. found, 390.0444.

6-(4-Chlorophenyl)-4-[(E,Z)-methanesulfonyloximino]-1,4,5,6-tetrahydropyridine-2-carboxylic acid methyl ester (21)

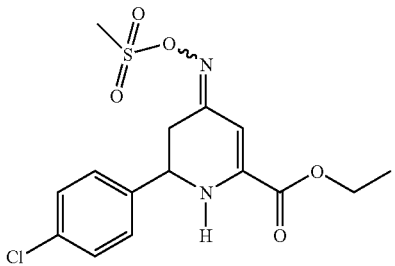 [SMILES: CCOC(=O)C1=CC(=NOS(C)(=O)=O)CC(c2ccc(Cl)cc2)N1]

Using the procedure of Example 10, 6-(4-chlorophenyl)-4-hydroxyimino-1,4,5,6-tetrahydropyridine-2-carboxylic acid ethyl ester (19; 13.0 g, 0.0442 mol), methanesulfonyl chloride (5.5 mL, 0.0707 mol), and triethylamine (12.3 mL, 0.0884 mol) gave an 8:1 mixture of isomers of 6-(4-chlorophenyl)-4-[(E,Z)-methanesulfonyloximino]-1,4,5,6-tetrahydropyridine-2-carboxylic acid ethyl ester (21; 10.5 g, 86%, 97% pure by HPLC) as an off-white solid: mp 113-115° C.; $^1$H NMR (400 MHz, CDCl$_3$) major isomer δ 7.45-7.29 (m, 4H), 6.36 (s, 1H), 5.59 (s, 1H), 4.56 (dd, J=11.7, 5.3 Hz, 1H), 4.35 (q, J=7.1, 1.3 Hz, 2H), 3.15 (s, 3H), 2.82-2.67 (m, 2H), 1.38 (t, J=7.1 Hz, 3H); HRMS-ESI (m/z): calcd for C$_{15}$H$_{12}$ClN$_2$O$_5$S, 372.055. found, 372.055.

Example 11

Preparation of 6-(4-chloro-2-fluoro-3-methoxyphenyl)-4-[(E,Z)-p-toluenesulfonyloximino]-1,4,5,6-tetrahydropyridine-2-carboxylic acid methyl ester (22)

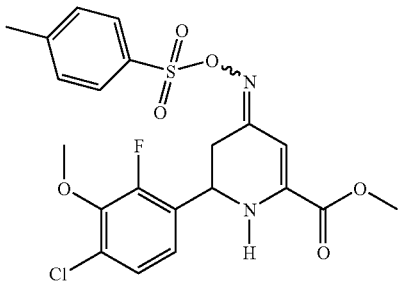

To a magnetically-stirred solution of 6-(4-chloro-2-fluoro-3-methoxyphenyl)-4-hydroxyimino-1,4,5,6-tetrahydropyridine-2-carboxylic acid methyl ester (18; 0.657 g, 0.002 mol) in pyridine (5 mL) cooled in an ice bath was added p-toluenesulfonyl chloride (0.572 g, 0.003 mol) over 5 min. After allowing the reaction mixture to warm to room temperature for 2 d, the solvent was removed under reduced pressure. The residue was dissolved in CH$_2$Cl$_2$ (50 mL), washed with saturated aqueous solutions of NaHCO$_3$ and NaCl, and dried (MgSO$_4$). Solvent removal gave a viscous orange oil (1.12 g). Trituration with ether/pentane gave a 4:1 mixture of isomers of 6-(4-chloro-2-fluoro-3-methoxyphenyl)-4-[(E,Z)-p-toluenesulfonyloximino]-1,4,5,6-tetrahydropyridine-2-carboxylic acid methyl ester (22; 0.818 g, 85%) as an off-white solid: mp 147-148° C.; $^1$H NMR (400 MHz, CDCl$_3$) δ 7.85 (d, J=8.3 Hz, 2H), 7.32 (d, J=8.0 Hz, 2H), 7.11 (dd, J=8.5, 1.7 Hz, 1H), 6.95 (dd, J=8.3, 7.2 Hz, 1H), 6.39 (s, 1H), 5.47 (s, 1H), 4.84 (dd, J=10.6, 4.5 Hz, 1H), 3.95 (d, J=1.1 Hz, 3H), 3.89 (s, 3H), 2.71 (ddd, J=26.3, 15.5, 7.7 Hz, 2H), 2.45 (s, 3H); HRMS-ESI (m/z): calcd for C$_{21}$H$_{20}$ClFN$_2$O$_6$S, 482.0709. found, 482.0701.

Example 12

Preparation of 6-(4-chloro-2-fluoro-3-methoxyphenyl)-4-[(E,Z)-methanesulfonyloximino]-1,4,5,6-tetrahydropyridine-2-carboxylic acid methyl ester (23)

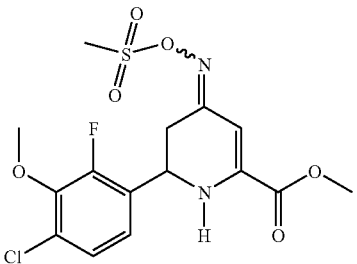 [SMILES: COC(=O)C1=CC(=NOS(C)(=O)=O)CC(c2ccc(Cl)c(OC)c2F)N1]

Step A: To a magnetically-stirred solution of 6-(4-chloro-2-fluoro-3-methoxyphenyl)-4-oxo-1,4,5,6-tetrahydropyridine-2-carboxylic acid methyl ester (16; 4.70 g, 0.015 mol) in MeOH (100 mL) at room temperature was added hydroxylamine hydrochloride (2.08 g, 0.03 mol), followed by pyridine (8 mL). After refluxing the mixture for 1 h, the solvent was removed under reduced pressure. The residue was dissolved in CH$_2$Cl$_2$ (100 mL) and was washed with saturated aqueous solutions of NaHCO$_3$ and NaCl. After drying (MgSO$_4$), solvent removal gave a 1:1 mixture of isomers of 6-(4-chloro-2-fluoorophenyl-3-methoxyphenyl)-4-hydroxyimino-1,4,5,6-tetrahydropyridine-2-carboxylic acid methyl ester (18; 4.95 g, 100% crude yield) as a yellow solid.

Step B: To a magnetically-stirred solution of 6-(4-chloro-2-fluoro-3-methoxyphenyl)-4-hydroxyimino-1,4,5,6-tetrahydropyridine-2-carboxylic acid methyl ester (18; 4.95 g, 0.015 mol) in pyridine (30 mL) cooled in an ice bath was added methanesulfonyl chloride (3.43 g, 0.03 mol) over 5 min. After allowing the reaction mixture to warm to room temperature for 2 d, solvent was removed under reduced pressure. The residue was dissolved in CH$_2$Cl$_2$ (100 mL), washed with saturated aqueous solutions of NaHCO$_3$ and NaCl, and dried (MgSO$_4$). Solvent removal gave a tacky light orange solid (5.5 g). Trituration with ether/pentane gave an 8:1 mixture of isomers of 6-(4-chloro-2-fluoro-3-methoxyphenyl)-4-[(E,Z)-methanesulfonyloximino]-1,4,5,6-tetrahydropyridine-2-carboxylic acid methyl ester (23; 4.14 g, 68%) as a white solid: mp 134-135° C.; $^1$H NMR (400 MHz, CDCl$_3$) major isomer δ 7.20 (dd, J=8.8, 1.3 Hz, 1H), 7.06 (dd, J=8.5, 6.7 Hz, 1H), 6.4 (s, 1H), 5.59 (br s, 1H), 4.93 (dd, J=10.8, 4.7 Hz, 1H), 3.96 (s, 3H), 3.90 (s, 3H), 3.15 (s, 3H), 2.81 (m, 2H); HRMS-ESI (m/z): calcd for C$_{15}$H$_{16}$ClFN$_2$O$_6$S, 406.040. found, 406.040.

6-(4-Chlorophenyl)-4-[(E,Z)-methanesulfonyloximino]-1,4,5,6-tetrahydro-pyridine-2-carboxylic acid methyl ester (24)

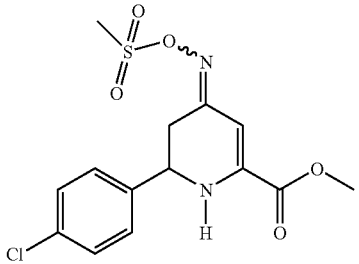 [SMILES: COC(=O)C1=CC(=NOS(C)(=O)=O)CC(c2ccc(Cl)cc2)N1]

Using the procedure of Example 12, 6-(4-chlorophenyl)-4-oxo-1,4,5,6-tetrahydropyridine-2-carboxylic acid methyl ester (13; 6.64 g, 0.025 mol), hydroxylamine hydrochloride (3.47 g, 0.05 mol), and pyridine (10 mL) gave an orange oil (9.1 g) after work-up. This material was redissolved in pyridine (40 mL) and treated with methanesulfonyl chloride (5.72 g, 0.05 mol) to provide a 4:1 mixture of isomers of 6-(4-chlorophenyl)-4-[(E,Z)-methanesulfonyloximino]-1,4,5,6-tetrahydropyridine-2-carboxylic acid methyl ester (24; 3.5 g, 39%, 95% pure by $^1$H NMR) as an off-white solid: mp 62-64° C.; $^1$H NMR (400 MHz, CDCl$_3$) major isomer δ 7.42-7.28 (m, 4H), 6.39 (s, 1H), 5.55 (s, 1H), 4.57 (dd, J=11.6, 5.1 Hz, 1H), 3.90 (s, 3H), 3.14 (s, 3H), 2.93-2.65 (m, 2H); minor isomer δ 7.45-7.28 (m, 4H), 6.15 (s, 1H), 5.23 (s, 1H), 4.41 (dd, J=13.4, 4.3 Hz, 1H), 3.90 (s, 3H), 3.30 (dd, J=17.2, 4.3 Hz, 1H), 3.15 (s, 3H), 2.56 (dd, J=17.1, 13.5 Hz, 1H); HRMS-ESI (m/z): calcd for C$_{14}$H$_{15}$ClN$_2$O$_5$S, 358.0384. found, 358.0385.

6-(4-Chloro-2-fluoro-3-methoxyphenyl)-4-[(E,Z)-methanesulfonyloximino]-1,4,5,6-tetrahydropyridine-2-carboxylic acid ethyl ester (25)

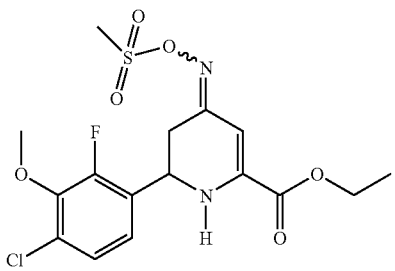 [SMILES: CCOC(=O)C1=CC(=NOS(C)(=O)=O)CC(c2ccc(Cl)c(OC)c2F)N1]

Using the procedure of Example 12, 6-(4-chloro-2-fluoro-3-methoxyphenyl)-4-oxo-1,4,5,6-tetrahydropyridine-2-carboxylic acid ethyl ester (14; 3.93 g, 0.012 mol), hydroxylamine hydrochloride (2.08 g, 0.03 mol), and pyridine (8 mL) gave a tacky orange solid (5.1 g) after work-up. This material was redissolved in pyridine (30 mL) and treated with methanesulfonyl chloride (2.75 g, 0.024 mol) to afford a 4:1 mixture of isomers of 6-(4-chloro-2-fluoro-3-methoxyphenyl)-4-[(E,Z)-methanesulfonyloximino]-1,4,5,6-tetrahydropyridine-2-carboxylic acid ethyl ester (25; 2.6 g, 52%, 95% pure by $^1$H NMR) as a white solid: mp 130-132° C.; $^1$H NMR (400 MHz, CDCl$_3$) δ 7.20 (dd, J=8.5, 1.5 Hz, 1H), 7.10-7.05 (m, 1H), 6.37 (s, 1H), 5.60 (s, 1H), 4.93 (dd, J=11.1, 4.4 Hz, 1H), 4.45-4.34 (m, 2H), 3.98 (d, J=1.1 Hz, 3H), 3.16 (s, 3H), 2.95-2.74 (m, 2H), 1.40 (d, J=7.1 Hz, 3H); HRMS-ESI (m/z): calcd for C$_{16}$H$_{18}$ClFN$_2$O$_6$S, 420.056. found, 420.056.

Example 13

Preparation of 3-chloro-6-(4-chloro-2-fluorophenyl)-4-[(E)-methanesulfonyloximino]-1,4,5,6-tetrahydropyridine-2-carboxylic acid methyl ester (26)

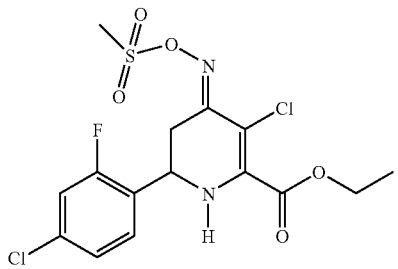 [SMILES: CCOC(=O)C1=C(Cl)/C(=N/OS(C)(=O)=O)CC(c2ccc(Cl)cc2F)N1]

To a magnetically-stirred solution of 6-(4-chloro-2-fluorophenyl)-4-[(E,Z)-methanesulfonyloximino]-1,4,5,6-tetrahydropyridine-2-carboxylic acid ethyl ester (20; 2.74 g, 0.007 mol) in CH$_2$Cl$_2$ (20 mL) cooled with an ice bath was added a solution of sulfuryl chloride (SO$_2$Cl$_2$, 0.94 g, 0.007 mol) in CH$_2$Cl$_2$ over 5 min. After allowing the reaction mixture to warm to room temperature for 1 h, CH$_2$Cl$_2$ (50 mL) was added. After washing the reaction mixture with a saturated aqueous solution of NaCl and drying (MgSO$_4$), solvent removal gave 3-chloro-6-(4-chloro-2-fluorophenyl)-4-[(E)-methanesulfonyloximino]-1,4,5,6-tetrahydropyridine-2-carboxylic acid ethyl ester (26; 2.91 g, 98%, 95% pure by $^1$H NMR) as a fluffy light yellow solid: mp 63-64° C.; $^1$H NMR (400 MHz, CDCl$_3$) δ 7.37 (t, J=8.1 Hz, 1H), 7.20 (dd, J=8.4, 1.7 Hz, 1H), 7.16 (dd, J=10.1, 2.0 Hz, 1H), 5.31 (s, 1H), 4.78 (dd, J=12.6, 4.5 Hz, 1H), 4.41 (q, J=7.1 Hz, 2H), 3.39 (dd, J=16.9, 4.4 Hz, 1H), 3.22 (s, 3H), 2.91-2.76 (m, 1H), 1.40 (t, J=7.1 Hz, 3H); HRMS-ESI (m/z): calcd for C$_{15}$H$_{15}$Cl$_2$FN$_2$O$_5$S, 425.240. found, 425.240.

3-Chloro-6-(4-chlorophenyl)-4-[(E)-methanesulfonyloximino]-1,4,5,6-tetrahydropyridine-2-carboxylic acid methyl ester (27)

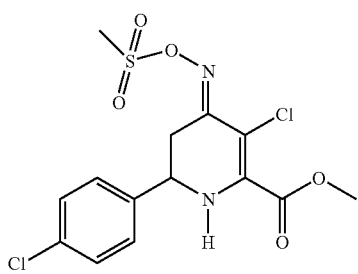 [SMILES: COC(=O)C1=C(Cl)/C(=N/OS(C)(=O)=O)CC(c2ccc(Cl)cc2)N1]

Using the procedure of Example 13, 6-(4-chlorophenyl)-4-[(E,Z)-methanesulfonyloximino]-1,4,5,6-tetrahydropyridine-2-carboxylic acid methyl ester (24; 2.78 g, 0.008 mol) and SO$_2$Cl$_2$ (1.08 g, 0.005 mol) in CH$_2$Cl$_2$ (25 mL) gave 3-chloro-6-(4-chlorophenyl)-4-[(E)-methanesulfonyloximino]-3-chloro-1,4,5,6-tetrahydropyridine-2-carboxylic acid methyl ester (27; 3.20 g, 99%, 95% pure by $^1$H NMR) as a fluffy light yellow solid: mp 60-62° C.; $^1$H NMR (400 MHz, CDCl$_3$) δ 7.41-7.29 (m, 4H), 5.33 (s, 1H), 4.44 (dd, J=13.8, 4.1 Hz, 1H), 3.94 (s, 3H), 3.40 (ddd, J=16.9, 4.2, 1.8 Hz, 1H), 3.21 (s, 3H), 2.88-2.57 (m, 1H); HRMS-ESI (m/z): calcd for C$_{15}$H$_4$Cl$_2$N$_2$O$_5$S, 391.9995. found, 391.9997.

3-Chloro-6-(4-chlorophenyl)-4-[(E)-methanesulfonyloximino]-1,4,5,6-tetrahydropyridine-2-carboxylic acid ethyl ester (28)

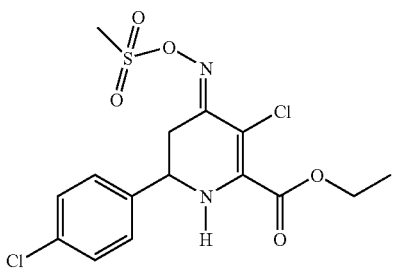 [SMILES: CCOC(=O)C1=C(Cl)/C(=N/OS(C)(=O)=O)CC(c2ccc(Cl)cc2)N1]

Using the procedure of Example 13, 6-(4-chlorophenyl)-4-[(E,Z)-methanesulfonyloximino]-1,4,5,6-tetrahydropyridine-2-carboxylic acid ethyl ester (21; 5.97 g, 0.016 mol) and SO$_2$Cl$_2$ (2.16 g, 0.016 mol) in CH$_2$Cl$_2$ (50 mL) gave 3-chloro-6-(4-chlorophenyl)-4-[(E)-methanesulfonyloximino]-1,4,5,6-tetrahydropyridine-2-carboxylic acid ethyl ester (28; 6.43 g, 99%, 92% pure by $^1$H NMR) as a fluffy light yellow solid: 57-59° C.; $^1$H NMR (400 MHz, CDCl$_3$) δ 7.35 (m, 4H), 5.35 (s, 1H), 4.44 (dd, J=13.0, 3.2 Hz, 1H), 4.39 (t, J=7.1 Hz, 2H), 3.39 (ddd, J=16.9, 4.2, 1.8 Hz, 1H), 3.22 (s, 3H), 2.65 (dd, J=16.9, 13.9 Hz, 1H), 1.40 (t, J=7.1 Hz, 3H); HRMS-ESI (m/z): calcd for C$_{125}$H$_{16}$Cl$_2$N$_2$O$_5$S, 406.015. found, 406.016.

3-Chloro-6-(4-chloro-2-fluoro-3-methoxyphenyl)-4-[(E)-methanesulfonyloximino]-1,4,5,6-tetrahydropyridine-2-carboxylic acid methyl ester (29)

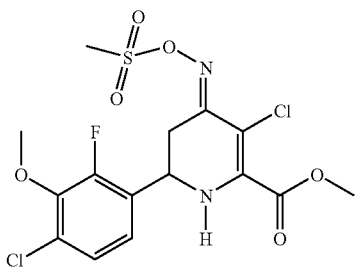 [SMILES: COC(=O)C1=C(Cl)/C(=N/OS(C)(=O)=O)CC(c2ccc(Cl)c(OC)c2F)N1]

Using the procedure of Example 13, 6-(4-chloro-2-fluoro-3-methoxyphenyl)-4-[(E,Z)-methanesulfonyloximino]-1,4,5,6-tetrahydropyridine-2-carboxylic acid methyl ester (23; 2.04 g, 0.005 mol) and SO$_2$Cl$_2$ (0.68 g, 0.005 mol) in CH$_2$Cl$_2$ (10 mL) gave 3-chloro-6-(4-chloro-2-fluoro-3-methoxyphenyl)-4-[(E)-methanesulfonyloximino]-1,4,5,6-tetrahydropyridine-2-carboxylic acid methyl ester (29; 2.18 g, 99%, 95% pure by $^1$H NMR) as a fluffy light yellow solid: mp 64-66° C.; $^1$H NMR (400 MHz, CDCl$_3$) δ 7.24 (dd, J=8.8, 1.3 Hz, 1H), 7.09 (dd, J=8.5, 6.7 Hz, 1H), 5.38 (s, 1H), 4.78 (dd, J=12.7, 4.5 Hz, 1H), 3.98 (s, 3H), 3.93 (s, 3H), 3.42 (dd, J=16.7, 4.5 Hz, 1H), 3.24 (s, 3H), 2.77 (dd, J=16.9, 12.8 Hz, 1H); HRMS-ESI (m/z): calcd for C$_{15}$H$_{15}$ClFN$_2$O$_5$S, 441.001. found, 441.002.

3-Chloro-6-(4-chloro-2-fluoro-3-methoxyphenyl)-4-[(E)-methanesulfonyloximino]-1,4,5,6-tetrahydropyridine-2-carboxylic acid ethyl ester (30)

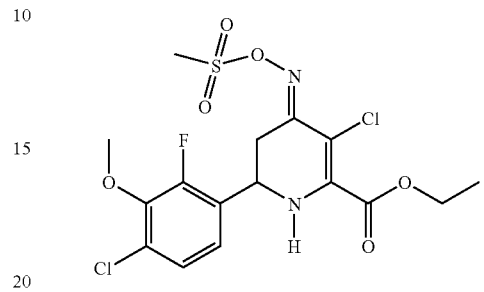

Using the procedure of Example 13, 6-(4-chloro-2-fluoro-3-methoxy-phenyl)-4-[(E,Z)-methanesulfonyloximino]-1,4,5,6-tetrahydropyridine-2-carboxylic acid methyl ester (25; 2.11 g, 0.005 mol) and SO$_2$Cl$_2$ (0.68 g, 0.005 mol) in CH$_2$Cl$_2$ (10 mL) gave 3-chloro-6-(4-chloro-2-fluoro-3-methoxyphenyl)-4-[(E)-methanesulfonyloximino]-1,4,5,6-tetrahydropyridine-2-carboxylic acid ethyl ester (30; 2.21 g, 97%, 95% pure by $^1$H NMR) as a fluffy light yellow solid: mp 60-62° C.; $^1$H NMR (400 MHz, CDCl$_3$) δ 7.21 (dd, J=8.5, 1.8 Hz, 1H), 7.08 (dd, J=8.6, 6.9 Hz, 1H), 5.32 (s, 1H), 4.78 (dd, J=12.8, 4.5 Hz, 1H), 4.41 (q, J=7.1 Hz, 2H), 3.99 (d, J=1.3 Hz, 3H), 3.41 (dd, J=16.9, 4.5 Hz, 1H), 3.23 (s, 3H), 2.76 (dd, J=11.7, 5.2 Hz, 1H), 1.40 (t, J=7.1 Hz, 3H); HRMS-ESI (m/z): calcd for C$_{16}$H$_{17}$Cl$_2$FNO$_6$S, 454.016. found, 454.017.

3-Chloro-6-(4-chloro-2-fluoro-3-methoxyphenyl)-4-[(E)-p-toluenesulfonyloximino]-1,4,5,6-tetrahydropyridine-2-carboxylic acid methyl ester (31)

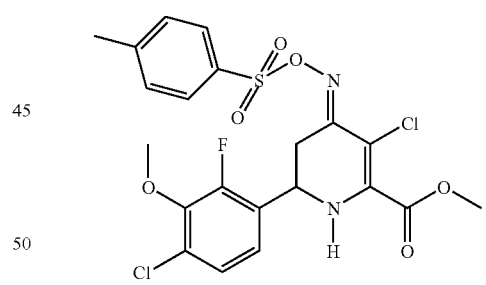

Using the procedure of Example 13, 6-(4-chloro-2-fluoro-3-methoxyphenyl)-4-[(E,Z)-p-toluenesulfonyloximino]-1,4,5,6-tetrahydropyridine-2-carboxylic acid methyl ester (22; 0.628 g, 0.0013 mol) and SO$_2$Cl$_2$ (0.175 g, 0.0013 mol) in CH$_2$Cl$_2$ (5 mL) gave 3-chloro-6-(4-chloro-2-fluoro-3-methoxyphenyl)-4-[(E)-p-toluenesulfonyloximino]-1,4,5,6-tetrahydropyridine-2-carboxylic acid methyl ester (31; 0.616 g, 98%, 95% pure by $^1$H NMR) as a fluffy light yellow solid: mp 62-64° C.; $^1$H NMR (400 MHz, CDCl$_3$) δ 7.91 (d, J=8.3 Hz, 2H), 7.34 (d, J=8.0 Hz, 2H), 7.16 (dd, J=8.5, 1.7 Hz, 1H), 7.01 (dd, J=8.4, 7.1 Hz, 1H), 5.25 (s, 1H), 4.70 (dd, J=12.6, 4.3 Hz, 1H), 3.97 (d, J=1.2 Hz, 3H), 3.91 (s, 3H), 3.33 (ddd, J=16.8, 4.4, 1.6 Hz, 1H), 2.88-2.64 (m, 1H), 2.45 (s, 3H); HRMS-ESI (m/z): calcd for C$_{21}$H$_{19}$Cl$_2$FN$_2$O$_5$S, 516.0322. found, 516.0319.

Example 14

Preparation of 3-bromo-6-(4-chloro-2-fluoro-3-methoxyphenyl)-4-[(E)-methanesulfonyloximino]-1,4,5,6-tetrahydropyridine-2-carboxylic acid methyl ester (32)

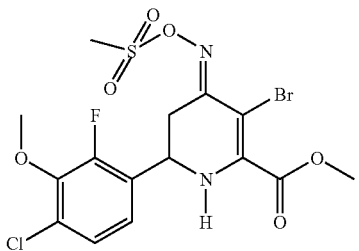 [SMILES: COC(=O)C1=C(Br)/C(=N/OS(C)(=O)=O)CC(c2ccc(Cl)c(OC)c2F)N1]

N-Bromosuccinimide (0.512 g, 2.88 mmol) was added to a solution of (6-(4-chloro-2-fluoro-3-methoxyphenyl)-4-[(E,Z)-methanesulfonyloximino]-1,4,5,6-tetrahydropyridine-2-carboxylic acid methyl ester (23; 1.17 g, 2.88 mmol) in $CH_2Cl_2$ (10 mL). The reaction mixture was stirred at ambient temperature for 1 h and it was then diluted with $CH_2Cl_2$ and washed with $H_2O$. The organic layer was separated and dried via Biotage Phase Separator SPE. The solvent was removed in vacuo to yield a brown oil (1.4 g). Purification by silica gel chromatography (40% EtOAc/10% $CH_2Cl_2$/50% pentane) provided 3-bromo-6-(4-chloro-2-fluoro-3-methoxyphenyl)-4-[(E)-methanesulfonyloximino]-1,4,5,6-tetrahydropyridine-2-carboxylic acid methyl ester (32; 1.17 g, 84%) as a yellow glass: $^1$H NMR (300 MHz, $CDCl_3$) δ 7.21 (dd, J=8.6, 1.8 Hz, 1H), 7.07 (dd, J=8.4, 6.7 Hz, 1H), 5.39 (s, 1H), 4.81 (d, J=12.2 Hz, 1H), 4.01-3.97 (m, 4H), 3.94 (d, J=2.0 Hz, 3H), 3.43 (dd, J=16.8, 2.8 Hz, 1H), 3.23 (d, J=1.9 Hz, 3H), 2.79 (dd, J=16.8, 12.7 Hz, 1H); HRMS-ESI (m/z): calcd for $C_{15}H_{17}BrClFN_2O_6S$, 485.9663. found, 485.9663.

Example 15

Preparation of 3-chloro-6-(4-chloro-2-fluoro-3-methoxyphenyl)-4-oxo-1,4,5,6-tetrahydropyridine-2-carboxylic acid methyl ester (33)

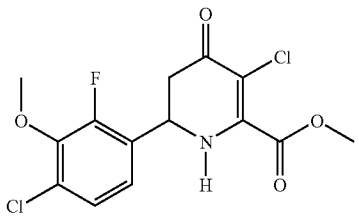 [SMILES: COC(=O)C1=C(Cl)C(=O)CC(c2ccc(Cl)c(OC)c2F)N1]

6-(4-Chloro-2-fluoro-3-methoxyphenyl)-4-oxo-1,4,5,6-tetrahydropyridine-2-carboxylic acid methyl ester (16; 483 mg, 1.54 mmol) was slurried in $CH_2Cl_2$ (10 mL) and cooled in an ice bath. A solution of $SO_2Cl_2$ (209 mg, 1.55 mmol) in $CH_2Cl_2$ (5 mL) was added dropwise. After 30 min, the reaction solution was quenched with 10% aqueous sodium bisulfite solution. The organic layer was separated, washed with saturated aqueous $NaHCO_3$ solution, $H_2O$ and brine and then dried ($MgSO_4$). The solution was evaporated to a yellow oil which was crystallized from cold methanol to give 3-chloro-6-(4-chloro-2-fluoro-3-methoxyphenyl)-4-oxo-1,4,5,6-tetrahydropyridine-2-carboxylic acid methyl ester (33; 0.437 g, 81%) as a light yellow solid: mp 127-129° C.; $^1$H NMR (300 MHz, $CDCl_3$) δ 7.20 (dd, $J_{F-H}$=1.5 Hz, $J_{H-H}$=8.1 Hz, 1H, aromatic), 7.10 (dd, $J_{F-H}$=6.9 Hz, $J_{H-H}$=8.1 Hz, 1H, aromatic), 5.82 (br s, 1H, NH), 5.10 (t, J=9.3 Hz, 1H, H6), 3.98 (d, $J_{F-H}$=1.5 Hz, 3H, $OCH_3$), 3.97 (s, 3H, $CO_2CH_3$), 2.88 (d, J=9 Hz, 2H, H5); ESIMS m/z 347.9 ([M+H]$^+$).

Example 16

Preparation of 3-chloro-6-(4-chloro-2-fluoro-3-methoxyphenyl)-4-hydroxyimino-1,4,5,6-tetrahydropyridine-2-carboxylic acid methyl ester (34)

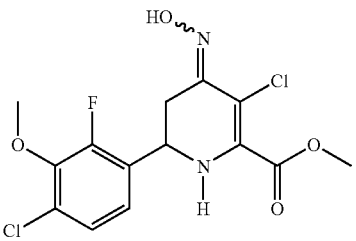 [SMILES: COC(=O)C1=C(Cl)C(=NO)CC(c2ccc(Cl)c(OC)c2F)N1]

3-Chloro-6-(4-chloro-2-fluoro-3-methoxyphenyl)-3-chloro-4-oxo-1,4,5,6-tetrahydropyridine-2-carboxylic acid methyl ester (33; 1.612 g, 4.63 mmol) was suspended in MeOH (20 mL). Hydroxylamine hydrochloride (966 mg, 13.9 mmol) was added followed by pyridine (3 mL). The reaction mixture was stirred for 18 h at room temperature and then for 4 h at 40° C. The solvent was removed by rotary evaporation. $H_2O$ (100 mL) was added, and the resulting solid was filtered, washed with $H_2O$ followed by MeOH to give 3-chloro-6-(4-chloro-2-fluoro-3-methoxyphenyl)-4-hydroxyimino-1,4,5,6-tetrahydropyridine-2-carboxylic acid methyl ester (34; 1.353 g, 81%) as a white powder: mp 174-176° C.; $^1$H NMR (300 MHz, DMSO-$d_6$) δ 11.23 (s, 1H, NOH), 7.35 (dd, $J_{F-H}$=1.5 Hz, $J_{H-H}$=8.7 Hz, 1H, aromatic), 7.17 (dd, $J_{F-H}$=$J_{H-H}$=8.7 Hz, 1H, aromatic), 6.93 (br s, 1H, NH), 4.69 (m, 1H, H6), 3.88 (s, 3H), 3.79 (s, 3H), 3.03 (dd, J=4.5, 16 Hz, 1H, H5a), 2.74 (dd, J=9.0, 16 Hz, 1H, H5b); Anal. Calcd for $C_{14}H_{13}Cl_2FN_2O_4$: C, 46.30; H, 3.61; N, 7.71. Found: C, 46.77; H, 3.64; N, 7.42.

Example 17

Preparation of 3-chloro-6-(4-chloro-2-fluoro-3-methoxyphenyl)-4-[(E)-acetoxyoximino]-3-chloro-1,4,5,6-tetrahydropyridine-2-carboxylic acid methyl ester (35)

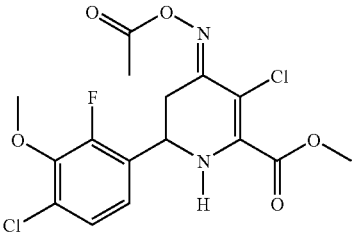 [SMILES: COC(=O)C1=C(Cl)/C(=N/OC(C)=O)CC(c2ccc(Cl)c(OC)c2F)N1]

3-Chloro-6-(4-chloro-2-fluoro-3-methoxyphenyl)-3-chloro-4-hydroxyimino-1,4,5,6-tetrahydropyridine-2-carboxylic acid methyl ester (34, 756 mg, 2.08 mmol) was slurried in glacial acetic acid (10 mL). Acetic anhydride (241 mg, 2.36 mmol) was added dropwise at room temperature. The reaction mixture was heated at 80° C. for 2 h. The solution was concentrated under vacuum, and the residue was dissolved in $CH_2Cl_2$ (50 mL) and washed with saturated aqueous $NaHCO_3$ solution. The extracts were washed with brine, dried ($MgSO_4$) and evaporated to give 3-chloro-6-(4-chloro-2-fluoro-3-methoxyphenyl)-4-[(E)-acetoxyoximino]-3-chloro-1,4,5,6-tetrahydropyridine-2-carboxylic acid methyl ester (35; 842 mg, 99%) as a light orange solid: $^1H$ NMR (400 MHz, $CDCl_3$) δ 7.21 (dd, $J_{F-H}$=1.5 Hz, $J_{H-H}$=8.4 Hz, 1H, aromatic), 7.11 (dd, $J_{F-H}$=6.9 Hz, $J_{H-H}$=8.4 Hz, 1H, aromatic), 5.24 (br s, 1H, NH), 4.76 (dd, J=4.2, 12.3 Hz, 1H, $H5_a$), 3.98 (d, $J_{F-H}$=1.5 Hz, 3H, OMe), 3.94 (s, 3H, $CO_2Me$), 3.40 (ddd, $J_{F-H}$=1.8 Hz, $J_{H-H}$=4.2, 16.5 Hz, 1H, H6), 2.72 (dd, J=12.3, 16.5 Hz, 1H, $H5_b$), 2.23 (s, 3H, NOAc). HRMS calcd for $C_{16}H_{15}Cl_2FN_2O_5$: 404.034. Found: 404.034.

Example 18

Preparation of Herbicidal Compositions

In the following illustrative compositions, parts and percentages are by weight (wt %).

| EMULSIFIABLE CONCENTRATES | |
|---|---|
| | WT % |
| Formulation A | |
| Compound 26 | 26.2 |
| Polyglycol 26-3 Nonionic emulsifier-(di-sec-butyl)-phenyl-poly(oxypropylene)block polymer with (oxyethylene). The polyoxythelene content is about 12 moles. | 5.2 |
| Witconate P12-20 (Anionic emulsifier-calcium dodecylbenzene sulfonate-60 wt % active) | 5.2 |
| Aromatic 100 (Xylene range aromatic solvent) | 63.4 |
| Formulation B | |
| Compound 28 | 3.5 |
| Sunspray 11N (paraffin oil) | 40.0 |
| Polyglycol 26-3 | 19.0 |
| Oleic acid | 1.0 |
| Xylene range aromatic solvent | 36.5 |
| Formulation C | |
| Compound 31 | 13.2 |
| Stepon C-65 | 25.7 |
| Ethomeen T/25 | 7.7 |
| Ethomeen T/15 | 18.0 |
| Xylene range aromatic solvent | 35.4 |
| Formulation D | |
| Compound 30 | 30.0 |
| Agrimer Al-10LC (emulsifier) | 3.0 |
| N-methyl-2-pyrrolidone | 67.0 |
| Formulation E | |
| Compound 30 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

| WETTABLE POWDERS | |
|---|---|
| | WT % |
| Formulation F | |
| Compound 27 | 26.0 |
| Polyglycol 26-3 | 2.0 |
| Polyfon H | 4.0 |
| Zeosyl 100 (Precipitated hydrated $SiO_2$) | 17.0 |
| Barden clay + inerts | 51.0 |
| Formulation G | |
| Compound 29 | 62.4 |
| Polyfon H (sodium salt of lignin sulfonate) | 6.0 |
| Sellogen HR (sodium naphthalene sulfonate) | 4.0 |
| Zeosyl 100 | 27.6 |
| Formulation H | |
| Compound 31 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

| WATER DISPERSIBLE GRANULES | |
|---|---|
| Formulation I | WT % |
| Compound 26 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

| GRANULES | |
|---|---|
| Formulation J | WT % |
| Compound 29 | 5.0 |
| Celetom MP-88 | 95.0 |

The active ingredient is applied in a polar solvent such as N-methylpyrrolidinone, cyclohexanone, gamma-butyrolactone, etc. to the Celetom MP 88 carrier or to other suitable carriers. The resulting granules can be applied by hand, granule applicator, airplane, etc. in order to control weeds.

| Formulation K | WT % |
|---|---|
| Compound 27 | 1.0 |
| Polyfon H | 8.0 |

-continued

| Formulation K | WT % |
|---|---|
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

The active ingredient is dissolved in an appropiate amount of water and the additional monoethanolamine is added as a buffer. A water-soluble surfactant may be added. Other aids may be incorporated to improve physical, chemical and/or formulation properties.

Example 19

Evaluation of Herbicidal Activity

Post-emergent Test I: Weed seeds were obtained from commercial suppliers and planted into 5"-round pots containing soilless media mix (Metro-Mix 360®, Sun Gro Horticulture Canada CM Ltd. Vancouver, British Columbia) 8-12 d prior to application and cultured in a greenhouse equipped with supplemental light sources to provide a 16 h photoperiod at 24-29° C. All pots were surface irrigated.

Compounds were dissolved in a 97:3 v/v (volume per volume) mixture of acetone and dimethyl sulfoxide (DMSO) and diluted to the appropriate concentration in a final application solution containing water, acetone, isopropyl alcohol, DMSO and Agri-dex (crop oil concentrate) in a 59:23:15:1.0:1.5 v/v ratio and 0.02% w/v (weight per volume) of Triton X-155 to obtain the spray solution containing the highest application rate. The high application rate was serial diluted with the above application solution to provide delivery of the compound at rates 1/2×, 1/4× and 1/8× of the highest rate (equivalent to 4.0, 2.0, 1.0, and 0.5 kg/ha, respectively).

Formulated compound (2.7 mL) was applied using a DeVilbiss® compressed air sprayer at 2-4 pounds per square inch (psi) (0.29-0.58 kilopascals (kPa)). Following treatment, pots were allowed to dry before being returned to the greenhouse for the duration of the experiment and subirrigated as needed. All pots were fertilized one time per week by subirrigating with Peters Peat-Lite Special® fertilizer (20-10-20).

Phytotoxicity ratings were obtained 10 d after treatment. All evaluations were made on a scale of 0 to 100 where 0 represents no activity and 100 represents complete plant death. Some of the compounds tested, application rates employed, plant species tested, and results are given in Tables 1.

TABLE 1

Post-emergent Test I Control of Weeds

| | Rate g ai/ha | AMARE | HELAN | IPOHE | AVEFA | SETFA |
|---|---|---|---|---|---|---|
| 26 | 3760 | NT | 100 | 100 | 95 | 100 |
| 27 | 3960 | 100 | 95 | 85 | 75 | 90 |
| 29 | 4000 | 100 | 90 | 95 | 30 | 90 |
| 30 | 3400 | 100 | 90 | 95 | 30 | 85 |
| 31 | 4000 | NT | 90 | 90 | 40 | 80 |

AMARE: pigweed (*Amaranthus retroflexus*)
HELAN: sunflower (*Helianthus annuus*)
IPOHE: ivyleaf morningglory (*Ipomoea hederacea*)
AVEFA: wild oat (*Avena fatua*)
SETFA: giant foxtail (*Setaria faberi*)

Pre-emergent Test I: Weed seeds were obtained from commercial suppliers and planted into round plastic pots (5-inch diameter) containing silt loam soil (23% sand, 52% silt, 29% clay, 2.9% organic matter, CEC 16.6, pH 7.2). After planting, all pots were subirrigated 16 h prior to compound application.

Compounds were dissolved in a 97:3 v/v mixture of acetone and DMSO and diluted to the appropriate concentration in a final application solution containing water, acetone, isopropyl alcohol, DMSO and Agri-dex (crop oil concentrate) in a 59:23:15:1.0:1.5 v/v ratio and 0.02% w/v of Triton X-155 to obtain the spray solution containing the highest application rate. The high application rate was serial diluted with the above application solution to provide delivery of the compound at rates 1/2×, 1/4× and 1/8× of the highest rate (equivalent to 4.0, 2.0, 1.0, and 0.5 kg/ha, respectively).

Formulated compound (2.7 mL) was pipetted evenly over the soil surface followed by incorporation with water (15 mL). Following treatment, pots were returned to the greenhouse for the duration of the experiment. The greenhouse was programmed for an approximate 15 h photoperiod which was maintained at about 23-29° C. during the day and 22-28° C. during the night. Nutrients and water were added on a regular basis through surface irrigation and supplemental lighting was provided with overhead metal halide 1000-Watt lamps as necessary.

Herbicidal effect ratings were obtained 14 d after treatment. All evaluations were made relative to appropriate controls on a scale of 0 to 100 where 0 represents no herbicidal effect and 100 represents plant death or lack of emergence from the soil. Some of the compounds tested, application rates employed, plant species tested, and results are given in Tables 2.

TABLE 2

Pre-emergent Test I Control of Weeds

| | Rate g ai/ha | AMARE | HELAN | IPOHE | AVEFA | SETFA |
|---|---|---|---|---|---|---|
| 26 | 3760 | 100 | 70 | 100 | 10 | 70 |
| 27 | 3960 | 100 | 100 | 100 | 20 | 100 |
| 29 | 4000 | 100 | 80 | 95 | 30 | 60 |
| 30 | 3400 | 100 | 100 | 100 | 95 | 100 |
| 31 | 4000 | 100 | 100 | 100 | 10 | 10 |

AMARE: pigweed (*Amaranthus retroflexus*)
HELAN: sunflower (*Helianthus annuus*)
IPOHE: ivyleaf morningglory (*Ipomoea hederacea*)
AVEFA: wild oat (*Avena fatua*)
SETFA: giant foxtail (*Setaria faberi*)

Post-emergent Test II: Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2×, 1/4×, 1/8× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Tables 3.

TABLE 3

Post-emergent Test II Control of Weeds

| | Rate g ai/ha | ORYSA | CHEAL | POLCO | ABUTH | ECHCG |
|---|---|---|---|---|---|---|
| 29 | 140 | 0 | 100 | 90 | 100 | 100 |
| 32 | 140 | 15 | 100 | 90 | 100 | 90 |
| 35 | 70 | 0 | 100 | 100 | 100 | 90 |

ORYSA: rice (*Oryza sativa*)
CHEAL: lambsquarters (*Chenopodium album*)
POLCO: bindweed (*Polygonum convolvulus*)
ABUTH: velvetleaf (*Abutilon theophrasti*)
ECHCG: barnyardgrass (*Echinochloa crus-galli*)

What is claimed is:

1. A compound of the Formula I

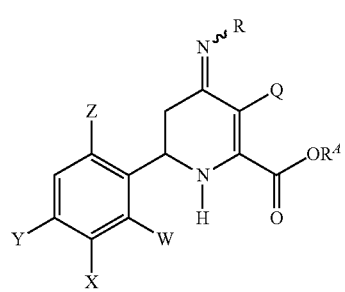

wherein
R represents —OS(O)$_2$R$^1$, —OC(O)R$^1$, —OC(O)OR$^1$;
R$^1$ represents C$_1$-C$_4$ alkyl or unsubstituted or substituted phenyl;
Q represents Cl or Br; and W represents H, F or Cl;
X represents H, F, Cl or C$_1$-C$_4$ alkoxy;
Y represents halogen; and
Z represents H or F; and
R$^A$ represents H, C$_1$-C$_{12}$ alkyl, C$_3$-C$_{12}$ alkenyl, or C$_3$-C$_{12}$ alkynyl.

2. The compound of claim 1, wherein W represents H or F, X represents H, F or C$_1$-C$_4$ alkoxy, Y represents Cl and Z represents H.

3. An herbicidal composition comprising an herbicidally effective amount of a compound as claimed in claim 1, in admixture with an agriculturally acceptable adjuvant or carrier.

4. A method of controlling undesirable vegetation which comprises contacting the vegetation or locus thereof with or applying to soil to prevent the emergence of vegetation an herbicidally effective amount of a compound of claim 1.

5. The compound of claim 1, wherein R is —OS(O)$_2$CH$_3$.

6. The compound of claim 1, wherein R is —OC(O)CH$_3$.

7. The compound of claim 1, wherein Z is H.

8. The compound of claim 1, wherein W is F, X is methoxy, Y is Cl, and Z is H.

9. The compound of claim 1, which R$^A$ is methyl or ethyl.

10. The compound of claim 1, wherein the compound is:

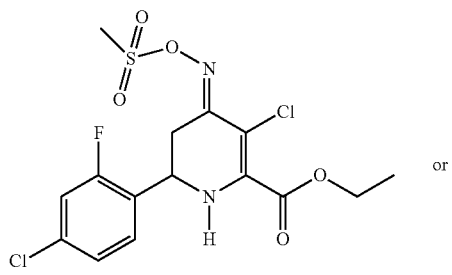 or

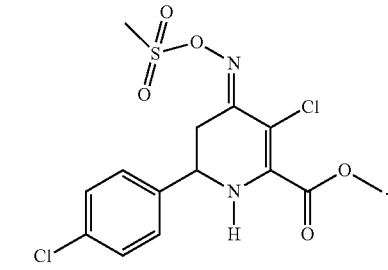.

11. The compound of claim 1, wherein the compound is:

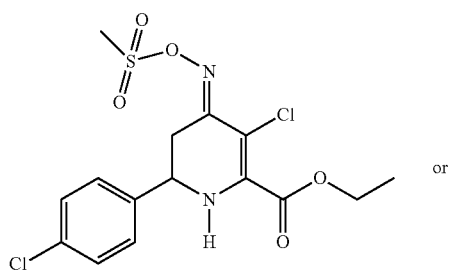 or

-continued
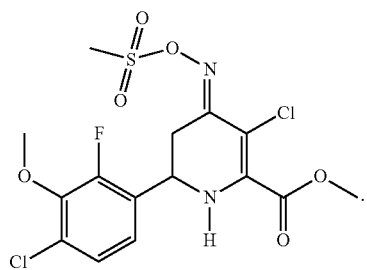
12. The compound of claim 1, wherein the compound is:
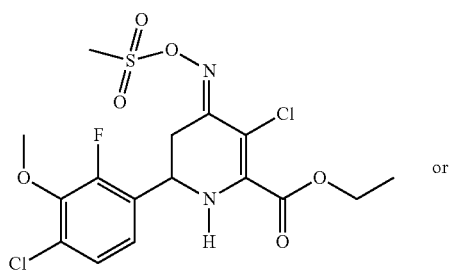
or
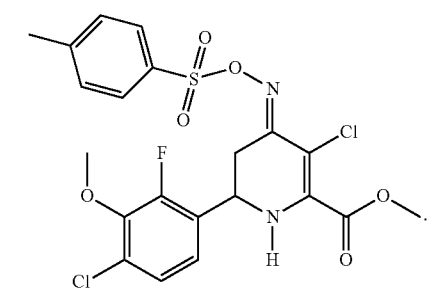
13. The compound of claim 1, wherein the compound is:
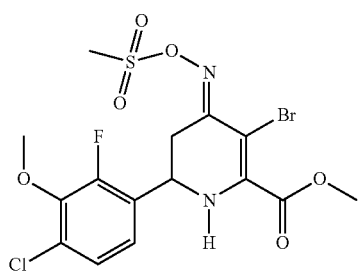
or
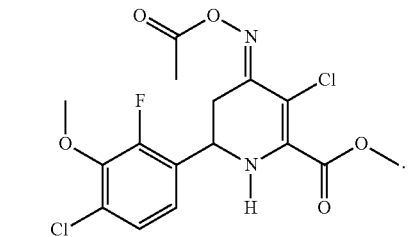
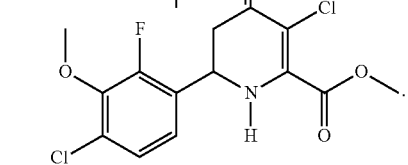
14. The composition of claim 3, wherein W represents H or F, X represents H, F or $C_1$-$C_4$ alkoxy, Y represents Cl and Z represents H.
15. The composition of claim 3, wherein the compound is:
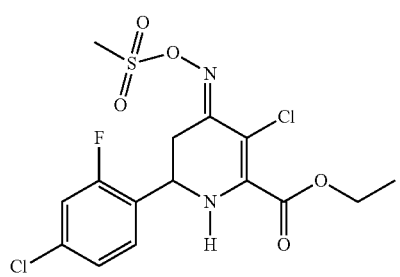
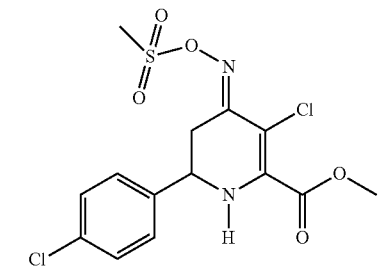
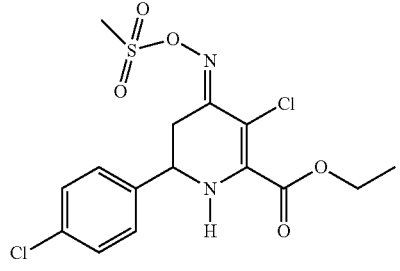
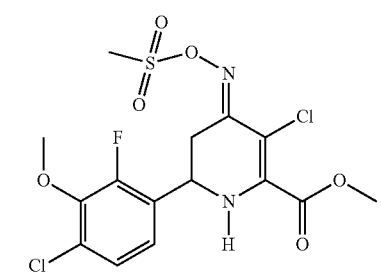
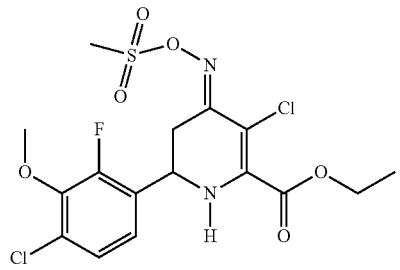
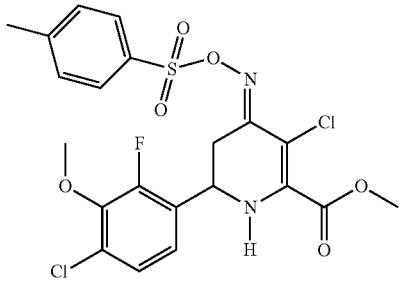

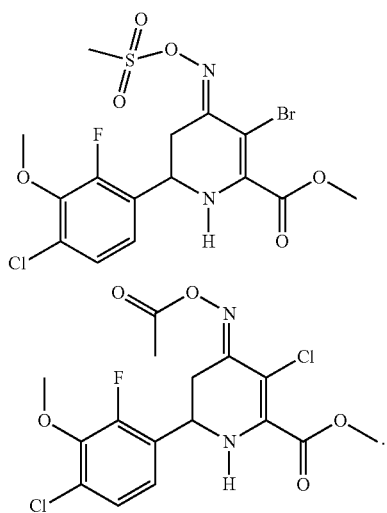

16. The method of claim 4, wherein W represents H or F, X represents H, F or $C_1$-$C_4$ alkoxy, Y represents Cl and Z represents H.

17. The method of claim 4, wherein the compound is:

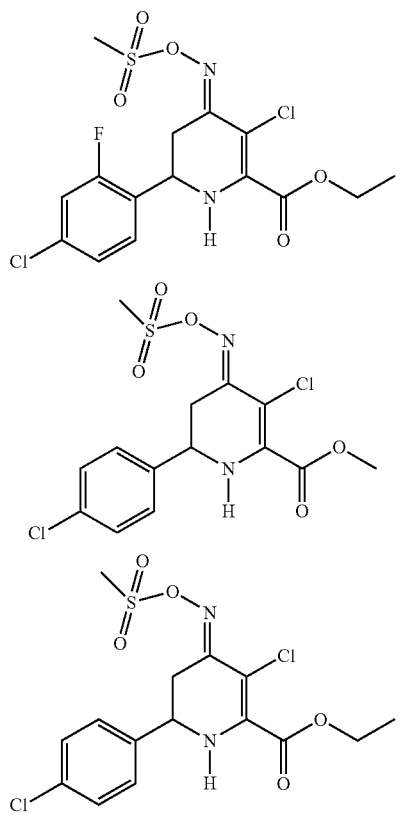

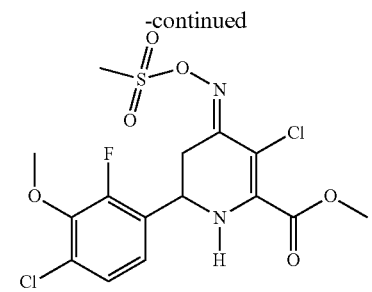

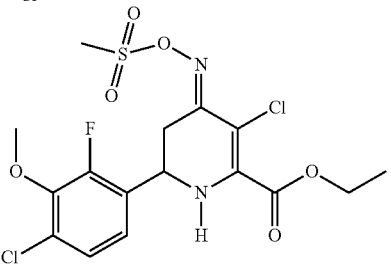

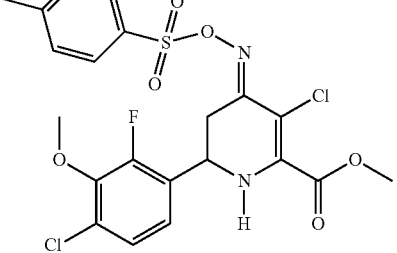

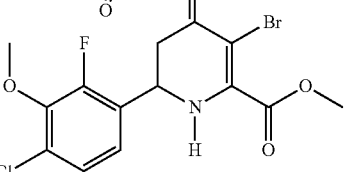

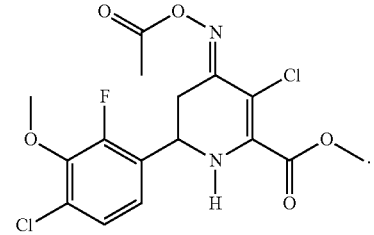

18. The method of claim 4, wherein the undesirable vegetation is pigweed, sunflower, ivyleaf morningglory, wild oat, giant foxtail, lambsquarters, bindweed, velvetleaf, or barnyardgrass.

19. The method of claim 4, wherein the contacting is performed pre-emergently.

20. The method of claim 4, wherein the contacting is performed post-emergently.

* * * * *